United States Patent
Lavon et al.

(10) Patent No.: US 12,247,216 B2
(45) Date of Patent: Mar. 11, 2025

(54) PLURIPOTENT CELL AGGREGATES AND USE THEREOF

(71) Applicant: ALEPH FARMS LTD., Rehovot (IL)

(72) Inventors: Neta Lavon, Ness Ziona (IL); Didier Toubia, Raanana (IL); Anna Bodanovsky, Tel Aviv (IL)

(73) Assignee: ALEPH FARMS LTD., Rehovot (IL)

( * ) Notice: Subject to any disclaimer, the term of this patent is extended or adjusted under 35 U.S.C. 154(b) by 716 days.

(21) Appl. No.: 17/610,485

(22) PCT Filed: May 14, 2020

(86) PCT No.: PCT/IL2020/050528
§ 371 (c)(1),
(2) Date: Nov. 11, 2021

(87) PCT Pub. No.: WO2020/230138
PCT Pub. Date: Nov. 19, 2020

(65) Prior Publication Data
US 2022/0220439 A1     Jul. 14, 2022

Related U.S. Application Data

(60) Provisional application No. 62/847,345, filed on May 14, 2019.

(51) Int. Cl.
*C12N 5/0735*        (2010.01)

(52) U.S. Cl.
CPC ...... *C12N 5/0606* (2013.01); *C12N 2501/115* (2013.01); *C12N 2501/415* (2013.01); *C12N 2510/00* (2013.01); *C12N 2511/00* (2013.01)

(58) Field of Classification Search
CPC .................................................. C12N 5/0606
See application file for complete search history.

(56) References Cited

U.S. PATENT DOCUMENTS

| | | | |
|---|---|---|---|
| 6,835,390 | B1 | 12/2004 | Vein |
| 9,752,122 | B2 | 9/2017 | Marga |
| 9,834,749 | B2 | 12/2017 | Amit |
| 9,944,894 | B2 | 4/2018 | Davis |

(Continued)

FOREIGN PATENT DOCUMENTS

| | | | |
|---|---|---|---|
| AU | 2014200783 B2 | 5/2016 | |
| AU | 2017225083 B2 | 11/2019 | |

(Continued)

OTHER PUBLICATIONS

Lewandowski et at., "Techniques for the induction of human pluripotent stem cell differentiation towards cardiomyocytes," J Tissue Eng Regen Med 11:1658-1674, 2017.*

(Continued)

*Primary Examiner* — Rosanne Kosson
(74) *Attorney, Agent, or Firm* — Rodney J. Fuller; Booth Udall Fuller, PLC

(57) ABSTRACT

The present invention relates to compositions and methods for mass production of pluripotent stem cells derived from non-human-animal, particularly in a form of aggregates suitable for a variety of uses, particularly to mass production of aggregates of bovine-derived pluripotent stem cells for use in cell grown meat cultures and in production of cell based meat products.

14 Claims, 13 Drawing Sheets

(56) References Cited

U.S. PATENT DOCUMENTS

| | | | |
|---|---|---|---|
| 10,669,524 | B2 | 6/2020 | Forgacs |
| 10,669,525 | B2 | 6/2020 | Yokoyama |
| 2014/0093618 | A1 | 4/2014 | Forgacs |
| 2018/0371036 | A1 | 12/2018 | Yamanaka |
| 2019/0078057 | A1 | 3/2019 | Jaenisch |

FOREIGN PATENT DOCUMENTS

| | | |
|---|---|---|
| CN | 105555949 A | 5/2016 |
| GB | 2617629 A | 10/2023 |
| JP | 2014521336 A | 8/2014 |
| JP | 2019162054 A | 9/2019 |
| WO | 9003432 A1 | 4/1990 |
| WO | 9931223 A1 | 6/1999 |
| WO | 2006041429 A2 | 4/2006 |
| WO | 2007069666 A1 | 6/2007 |
| WO | 2008015682 A2 | 2/2008 |
| WO | 2008124133 A1 | 10/2008 |
| WO | 2008136733 A1 | 11/2008 |
| WO | 2009032194 A1 | 3/2009 |
| WO | 2009075119 A1 | 6/2009 |
| WO | 2009133971 A1 | 11/2009 |
| WO | 2009152529 A2 | 12/2009 |
| WO | 2009157593 A1 | 12/2009 |
| WO | 2010013845 A1 | 2/2010 |
| WO | 2010017562 A2 | 2/2010 |
| WO | 2010124091 A1 | 10/2010 |
| WO | 2010124290 A2 | 10/2010 |
| WO | 2010137746 A1 | 12/2010 |
| WO | 2011016588 A1 | 2/2011 |
| WO | 2011158960 A1 | 12/2011 |
| WO | 2012036299 A1 | 3/2012 |
| WO | 2012060473 A1 | 5/2012 |
| WO | 2012074117 A1 | 6/2012 |
| WO | 2012087965 A2 | 6/2012 |
| WO | 2013014929 A1 | 1/2013 |
| WO | 2013159103 A1 | 10/2013 |
| WO | 2013173248 A2 | 11/2013 |
| WO | 2013176233 A1 | 11/2013 |
| WO | 2013188679 A1 | 12/2013 |
| WO | 2014039938 A1 | 3/2014 |
| WO | 2014189144 A1 | 11/2014 |
| WO | 2014200030 A1 | 12/2014 |
| WO | 2014200114 A1 | 12/2014 |
| WO | 2015056804 A1 | 4/2015 |
| WO | 2015066377 A1 | 5/2015 |
| WO | 2016210313 A1 | 12/2016 |
| WO | 2017124100 A1 | 7/2017 |
| WO | 2018011805 A2 | 1/2018 |
| WO | 2018015954 A1 | 1/2018 |
| WO | 2019016795 A1 | 1/2019 |
| WO | 2019140260 A1 | 7/2019 |
| WO | 2021207293 A1 | 10/2021 |
| WO | 2022104378 A1 | 5/2022 |
| WO | 2023003470 A1 | 1/2023 |
| WO | 2023003471 A1 | 1/2023 |

OTHER PUBLICATIONS

Anokye-Danso et al., (2011) Highly efficient miRNA-mediated reprogramming of mouse and human somatic cells to pluripotency. Cell Stem Cell 8(4): 376-388.

Beeravolu et al., (2017) Isolation and Characterization of Mesenchymal Stromal Cells from Human Umbilical Cord and Fetal Placenta. J Vis Exp 122: e55224; 13 pages.

Bogliotti et al., (2018) Efficient derivation of stable primed pluripotent embryonic stem cells from bovine blastocysts. Proc Natl Acad Sci U S A 115(9): 2090-2095.

Boroviak and Nichols (2017) Primate embryogenesis predicts the hallmarks of human naïve pluripotency. Development 144(2): 175-186.

Cao et al., (2012) Characterization of bovine induced pluripotent stem cells by lentiviral transduction of reprogramming factor fusion proteins. Int J Biol Sci 8(4): 498-511.

Castro Neto et al., (2005) Improvement in embryo recovery using double uterine flushing. Theriogenology 63(5): 1249-1255.

Dakhore et al., (2018) Human Pluripotent Stem Cell Culture: Current Status, Challenges, and Advancement. Stem Cells Int 2018: 7396905.

Davis et al., (2018) Automated Closed-System Expansion of Pluripotent Stem Cell Aggregates in a Rocking-Motion Bioreactor. SLAS Technol 23(4): 364-373.

Diecke et al., (2015) Novel codon-optimized mini-intronic plasmid for efficient, inexpensive, and xeno-free induction of pluripotency. Sci Rep 5: 8081; 9 pages.

Ezashi et al., (2012) Induced pluripotent stem cells from pigs and other ungulate species: an alternative to embryonic stem cells? Reprod Domest Anim 47 Suppl 4: 92-97.

Ezashi et al., (2016) Pluripotent Stem Cells from Domesticated Mammals. Annu Rev Anim Biosci 4: 223-253.

Han et al., (2011) Generation of induced pluripotent stem cells from bovine embryonic fibroblast cells. Cell Res 21(10): 1509-1512.

Huang et al., (2011) A virus-free poly-promoter vector induces pluripotency in quiescent bovine cells under chemically defined conditions of dual kinase inhibition. PLoS One 6(9): e24501; 14 pages.

Kahn (2014) Can we safely target the WNT pathway? Nat Rev Drug Discov 13(7): 513-532.

Kim et al., (2013) Modulation of β-catenin function maintains mouse epiblast stem cell and human embryonic stem cell self-renewal. Nat Commun 4: 2403; 11 pages.

Lei and Schaffer (2013) A fully defined and scalable 3D culture system for human pluripotent stem cell expansion and differentiation. Proc Natl Acad Sci U S A 110(52): E5039-E5048.

Li et al., (2018) A fully defined static suspension culture system for large-scale human embryonic stem cell production. Cell Death Dis 9(9): 892; 9 pages.

Li et al., (2018) Scalable and physiologically relevant microenvironments for human pluripotent stem cell expansion and differentiation. Biofabrication 10(2): 025006; 16 pages.

Ogorevc et al., (2016) Cellular reprogramming in farm animals: an overview of iPSC generation in the mammalian farm animal species. J Anim Sci Biotechnol 7: 10; 9 pages.

Poleganov et al., (2015) Efficient Reprogramming of Human Fibroblasts and Blood-Derived Endothelial Progenitor Cells Using Nonmodified RNA for Reprogramming and Immune Evasion. Hum Gene Ther 26(11): 751-766.

Roberts et al., (2015) Livestock models for exploiting the promise of pluripotent stem cells. ILAR J ;56(1): 74-82.

Song et al., (2012) Loss of wnt/β-catenin signaling causes cell fate shift of preosteoblasts from osteoblasts to adipocytes. J Bone Miner Res 27(11): 2344-2358.

Takahashi and Yamanaka (2006) Induction of pluripotent stem cells from mouse embryonic and adult fibroblast cultures by defined factors. Cell 126(4): 663-676.

Takahashi et al., (2007) Induction of pluripotent stem cells from adult human fibroblasts by defined factors. Cell 131(5): 861-872.

Talluri et al., (2015) Derivation and characterization of bovine induced pluripotent stem cells by transposon-mediated reprogramming. Cell Reprogram 17(2): 131-140.

Watanabe et al., (2005) Directed differentiation of telencephalic precursors from embryonic stem cells. Nat Neurosci 8 (3): 288-296.

Yoshida et al., (2009) Hypoxia enhances the generation of induced pluripotent stem cells. Cell Stem Cell 5(3): 237-241.

Yu et al., (2007) Induced pluripotent stem cell lines derived from human somatic cells. Science 318(5858): 1917-1920.

Zeng et al., (2018) MicroRNAs: Important Regulators of Induced Pluripotent Stem Cell Generation and Differentiation. Stem Cell Rev Rep 14(1): 71-81.

Zur Nieden et al., (2007) Embryonic stem cells remain highly pluripotent following long term expansion as aggregates in suspension bioreactors. J Biotechnol 129(3): 421-432.

"Epigenetics and Precision Medicine", (2017) Zhu Jingde, pp. 413-414, Shanghai Jiao Tong University Press. With machine translation.

(56) References Cited

OTHER PUBLICATIONS

Wu et al., (2015) An alternative pluripotent state confers interspecies chimaeric competency. Nature 521(7552): 316-321.

* cited by examiner

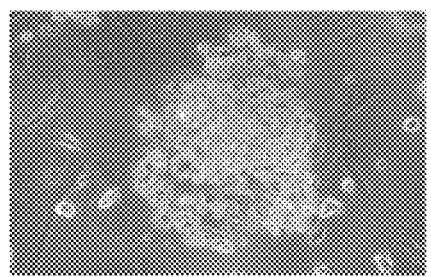 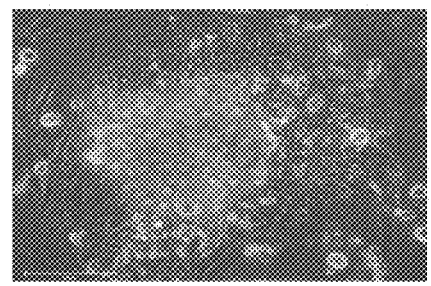
FIG. 1A  FIG. 1B
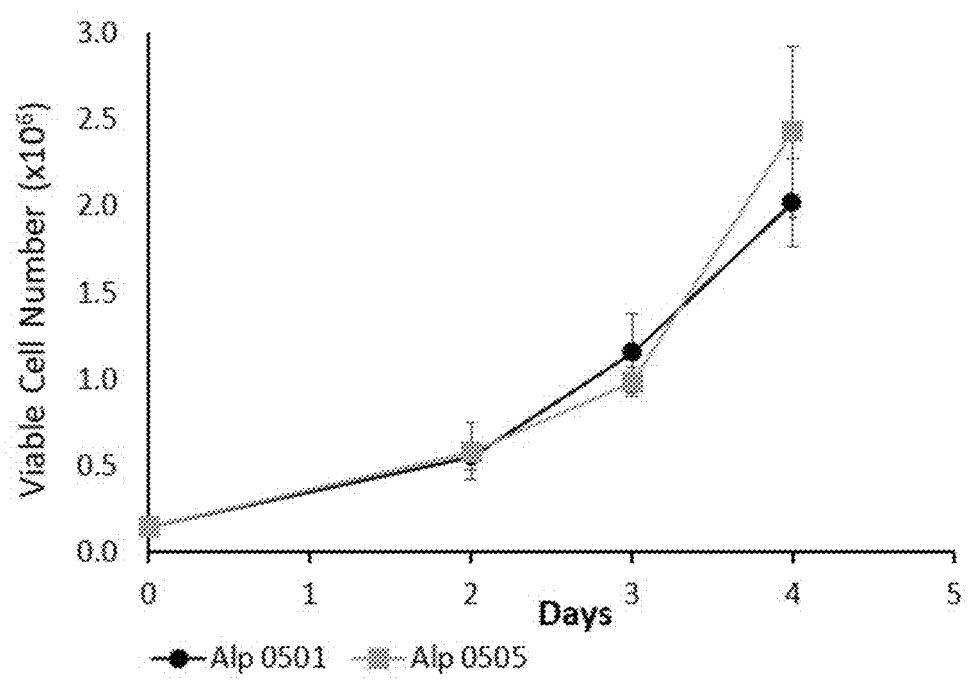
FIG. 2

PLURIPOTENT CELL AGGREGATES AND USE THEREOF

FIELD OF THE INVENTION

The present invention relates to compositions and methods for mass production of pluripotent stem cells derived from non-human-animal, particularly in a form of aggregates suitable for a variety of uses, particularly to mass production of aggregates of bovine-derived pluripotent stem cells for use in cell grown meat cultures and in production of cell based meat products.

BACKGROUND OF THE INVENTION

Many expendable resources are exploited in order to support livestock growth, specifically cattle for meat production, including water, grain, land and energy. The world's rapidly growing population will lead to a further increase in the use of said invaluable assets. Therefore, producing meat and meat products in ways that will downsize the cattle amount required to feed the entire population is most desirable. Replacing cattle as the main meat source is also ethically beneficial since it will prevent the crowded inhabitant and sometimes inappropriate conditions afflicted upon the cattle subjects. For this reason, cell grown meat products might also be potentially consumed by people who abstains meat for humanitarian reasons. Cell based meat (also referred to as cultured meat, cultivated meat, cell grown meat, clean meat, engineered meat, in-vitro meat and the like) is also a way to control consumed food content; nowadays, much of the cattle are being administered with growth hormones, which ends up on the consumer plates. Also, producing meat in culture will enable improving the nutritional values of the meat and making it healthier, via a control of protein content, fat amount and composition, iron, vitamin B12, zinc levels etc. In addition, consuming meat produced in bioreactors (or other cultivation systems) under strict regulations and clean conditions is less likely to transmit microbial contaminations and is therefore safer for consumption.

Pluripotent stem cells (PSCs) are cells that have the capacity to self-renew by dividing while keeping the capability to differentiate to every cell type in the body. Both embryonic stem cells (ESCs) and induced pluripotent stem cells (iPSCs) are pluripotent stem cells. ESCs are typically derived from the cell population in the inner cell mass of pre-implantation blastocysts. Induced pluripotent stem cells (iPSCs) are a type of PSCs, which are generated from somatic differentiated cells reprogrammed to recover their pluripotency characteristics. Bogliotti et al. (PNAS. 2018 11 (9): 2090-2095) described that by employing a culture system containing fibroblast growth factor 2 (also known as basic fibroblast growth factor, bFGF) and an inhibitor of the canonical Wnt-signaling pathway, pluripotent bovine ESCs (bESCs) with stable morphology, transcriptome, karyotype, population-doubling time, pluripotency marker gene expression, and epigenetic features were derived.

Reprogramming cells into iPSCs was first described by Takahashi and Yamanaka in 2006 (Takahashi and Yamanaka, Cell 2006, 126: 663-76). Since then, a large number of publications described reprogramming stem cells to iPSCs, from various cell types in multiple species (Yu et al., Science 2007, 318: 1917-20; Takahashi et al., Cell 2007, 131:861-72; Ogorerc et al. J Anim Sci Biotechnol 2016, 7:10; Ezashi et al., Annu Rev Anim Biosci. 2016, 4:223-53). In bovine, fibroblasts had been reprogrammed to iPSCs using a combination of reprogramming factors by several methods, including retroviral/lentiviral transduction, poly-promotor plasmid and piggyBac transposon systems (Ogorevc 2016 ibid; Han et al, Cell Res. 2011, 21: 1509-12; Huang et al., Plos One 2011, 6:e24501; Cao et al., Int J Biol Sci. 2012, 8: 498-511; Talluri et al., Cell Reprogram. 2015, 17: 131-40; Ezashi et al. 2016, ibid). There are no reports of more up-to-date methods (e.g. non-integrating virus- or non-integrating episomal vector or mRNA-based methods) being used for reprogramming cells in farm animal species (Ogorevc 2016, ibid). In bovine cells the usage of mRNA, small molecules and proteins as the reprogramming factors has not been demonstrated.

International Patent Application Publication No. WO 1999/031223 discloses a process for production of a meat product comprising in vitro, industrial scale culturing of animal cells to provide three dimensional animal muscle tissue suited for human and/or animal consumption, optionally followed by further processing steps of the cell culture to a finished food product analogous to known processes for meat comprising food products without requiring deboning, removal of offal and/or tendon and/or gristle and/or fat. Preferably, the meat product comprises solidified cell tissue, said cells being selected from muscle cells, somite cells and stem cells. A meat product comprising the solidified cell tissue is also provided.

International Patent Application Publication No. WO 2006/041429 and U.S. Pat. No. 6,835,390 disclose a non-human tissue engineered meat product and a method for producing such meat product. The meat product comprises muscle cells that are grown ex vivo and is used for food consumption.

International Patent Application Publication No. WO 2010/017562 provides iPSCs, compositions containing same, methods for obtaining iPSCs, and methods for using the iPSCs. In addition, methods and materials for using iPSCs to repair tissue (e.g., cardiovascular tissue) in vivo as well as methods and materials for using such cells to assess their therapeutic potential in appropriate animal models are provided.

International Patent Application Publication No. WO 2013/188679 discloses methods of preparing iPSCs, wherein a combination of mRNA and miRNA is introduced into the cells.

International Patent Application Publication No. WO 2015/066377 discloses methods for producing cultured muscle tissue comprising modifying a self-renewing cell line of an animal species with a myogenic transcription factor to produce a myogenic-transcription-factor-modified cell line.

International Patent Application Publication No. WO 2018/011805 discloses a system for growing cells comprising a bioreactor chamber for growing the cells. The application further discloses an in-vitro method of generating an edible meat comprising culturing in a serum-free medium spontaneously immortalized fibroblasts under conditions suitable for converting the fibroblast into adipocytes and/or under conditions suitable for converting the fibroblast into myocytes, thereby producing the edible meat.

International Application Publication No. WO 2019/016795 discloses a method for producing an edible composition comprising incubating a three-dimensional porous scaffold and a plurality of cell types and inducing myoblasts differentiation into myotubes. The plurality of cell types includes myoblasts or progenitor cells thereof, at least one type of extracellular (ECM)-secreting cell and endothelial cells or progenitor cells thereof.

International Application Publication No. 2019/140260 published after the priority date of the present application discloses methods for obtaining ungulate embryonic stem cells (ESCs) derived from the inner cell mass of pre-implantation blastocysts or pluripotent cells from embryos, useful for genomic testing and selection as well as genetic engineering of domestic ungulates, and as an experimental tool for studying human diseases.

U.S. Pat. No. 9,944,894 discloses closed systems on rocking platform bioreactors for expansion and passaging of cell aggregates comprising stem cells and/or differentiated cells. Also disclosed methods that permits closed system serial passage expansion of pluripotent stem cells and/or progeny thereof with associated pluripotency markers and differentiation potential.

U.S. Pat. No. 9,834,749 discloses a method of expanding and maintaining human embryonic stem cells (ESCs) in an undifferentiated state by culturing the ESCs in a suspension culture under culturing conditions devoid of substrate adherence. Useful in generating lineage-specific cells from the ESCs. The patent also discloses method of deriving ESC lines in the suspension culture.

There remains an unmet need for compositions and methods to enable large-scale production of non-genetically modified (GM) cell-grown meat from cells derived from non-human-animals, particularly bovine.

SUMMARY OF THE INVENTION

The present invention provides compositions and method for mass production of non-human-animal derived pluripotent stem cells (PSCs), particularly in a form of homogenous, 3 dimensional (3D), non-genetically modified (GM) aggregates. The present invention provides hitherto not available continuous reservoir of non-human-animal derived PSCs that maintain their pluripotency in large-scale liquid culture conditions. The PSCs can be used in the growing industry of cell grown meat products as well as an experimental tool for the research of cell expansion and differentiation and in the development of new non-human-animal related drugs.

The present invention is based in part on the unexpected discovery that bovine-derived pluripotent stem cells, and/or embryonic stem cells (ESCs) derived from bovine embryos obtained by flushing procedure can grow and maintain pluripotency and further can form 3D homogenous aggregates under large-scale liquid culture conditions, when specific combination of growth factor(s) and small molecule(s) are added to the culture medium. The cells within the aggregates keep their pluripotency and division rate, such that the diameter of the aggregates increases, resulting in mass production of pluripotent stem cells to reach a final concentration of $10^9$ to $10^{12}$ cells per liter liquid culture, hitherto not been reported for non-human-animal derived cells.

Without wishing to be bound by any particular theory or mechanism of action the pluripotent stem cells mass production and aggregate formation may be attributed to the source of the non-human-animal cells, particularly bovine cells, the unique serum-free medium comprising a combination of growth factor(s) and small molecule(s), and further to the system growth setup, including the use of a closed system in which steps of cell aggregation and disaggregation take place and an incubation temperature compatible with non-human-animal body temperature.

In certain aspects, the 3D non-human-animal derived PSC aggregates of the invention are the source for cell grown meat products. According to certain exemplary embodiments, the PSCs are bovine-derived cells.

According to one aspect, the present invention provides a method of mass production of aggregates of non-genetically modified non-human-animal derived pluripotent stem cells (PSCs) comprising the steps of: (a) seeding at least one PSC in an expansion medium, the expansion medium is a serum-free liquid medium comprising a combination of the growth factor bFGF, at least one additional growth factor and/or at least one small molecule selected from the group consisting of an inhibitor of the Wnt-β-catenin signaling pathway, CHIR 99021 (C22H18C12N8), PD 0325901 (C16H14F3IN2O4), and A 83-01 (C25H19N5S), to form a suspension culture; and (b) growing the suspension culture under conditions enabling aggregate formation and aggregate expansion, thereby forming homogenous aggregates of said PSCs.

According to certain embodiments, the seeding and growing is within a vessel having walls of a material to which the PSCs and/or aggregates comprising same do not adhere. It is to be explicitly understood that the PSC aggregates are formed in the vessel without the addition of inactivated feeder cells, organic extracellular matrix, feeder cell conditioned medium and/or microcarriers. Accordingly, the PSCs and/or aggregates comprising same are free within the suspension culture and are not adhered to a surface. According to certain embodiments, the vessel is a bioreactor.

According to certain embodiments, the homogenous aggregates comprise at least 70% of cells expressing at least one pluripotency marker.

According to certain embodiments, the at least one pluripotency marker is selected from the group consisting of stage-specific embryonic antigen-4 (SSEA4), octamer-binding transcription factor 4 (Oct4), Sall4 transcription factor, Nanog homeobox transcription factor, translation factor Lin28A, DNA-methyltransferase Dnmt3b, and a combination thereof. Each possibility represents a separate embodiment of the present invention. According to certain exemplary embodiments, the pluripotency marker is SSEA4.

According to certain embodiments, step (b) of growing the suspension culture comprises the steps of disaggregating the formed homogenous aggregates into smaller aggregates and/or single cells and re-aggregating the smaller aggregates and/or single cells to re-form homogenous aggregates.

According to certain exemplary embodiments, disaggregating the homogenous aggregates comprises exposing said aggregates to a dissociation reagent and/or to a dissociation force. According to some embodiments, the dissociation reagent comprises at least one proteolytic enzyme, and optionally at least one DNA degrading enzyme and/or chelating agent. According to certain embodiments, the chelating agent is selected from EDTA and EGTA. According to some exemplary embodiments, the proteolytic enzyme is trypsin.

According to some embodiments, the dissociation force is a shear force. According to certain embodiments, the shear force rate is set by an impeller embedded within the vessel.

According to certain embodiments, the step of disaggregating further comprises washing the homogenous aggregates prior to exposing said aggregates to the dissociation reagent and/or dissociation force with an aqueous-based washing medium.

According to certain embodiments, the step of re-aggregating comprises seeding the smaller aggregates and/or single cells in the expansion medium.

According to certain embodiments, the steps of seeding and of re-aggregating further comprises adding an inhibitor of Rho-associated protein kinase (Rock) to the medium.

According to certain embodiments, the entire production of aggregates is performed in a closed system. The use of a closed system is of significant advantage in the mass production of PSC aggregates at a large-scale allowing to keep a sterile environment and automated process. According to certain embodiments, the steps or disaggregation and re-aggregation are performed within a separate vessel connected to the bioreactor in a form maintaining the closed system. According to certain embodiments, the vessel is a cell retention device.

According to certain embodiments, the steps of disaggregation and re-aggregation are repeated at least once, at least twice, at least 3 times, at least 4 times, at least 5 times and more. It is to be explicitly understood that the number of repeats may be indefinite and would depend on the number of PSCs required for the intended use. According to certain exemplary embodiments, when the PSCs aggregates are for the production of cell grown meat, aggregates formation and disaggregation is repeated to reach a final cell concentration of from about $10^6$ cells/ml to about $10^9$ cells/ml. According to certain embodiments, aggregate formation and disaggregation is repeated to reach a final cell concentration of from about $5\times10^6$ to about $5\times10^8$ cells/ml.

According to certain embodiments, the at least one additional growth factor is a protein of the transforming growth factor beta (TGF-β, TGFB) superfamily. According to certain embodiments, the TGF-β is selected from the group consisting of TGF-β-1, TGF-β-3, Activin-A and any combination thereof.

According to certain embodiments, the expansion medium comprises a combination comprising bFGF and TGF-β.

According to certain embodiments, the expansion medium comprises a combination consisting of bFGF and at least one additional growth factor. According to certain exemplary embodiments, the additional growth factor is a protein of the TGF-β superfamily. According to certain embodiments, the TGF-β is selected from the group consisting of TGF-β-1, TGF-β-3, Activin-A and any combination thereof.

According to certain embodiments, the expansion medium comprises a combination consisting of bFGF and at least one small molecule.

According to certain embodiments, the inhibitor of the Wnt-β-catenin signaling pathway is selected from the group consisting of IWR1, JW67, NSC668036, KY02111, niclosamide, DKK1 or si-Beta-Catenin, porcupine inhibitor, and IWP-2. Each possibility represents a separate embodiment of the present invention.

According to certain exemplary embodiments, the inhibitor of the Wnt-β-catenin signaling pathway is IWR1.

According to certain embodiments, the expansion medium comprises a combination of the growth factors bFGF and a protein of the TGF-β superfamily, and a small molecule selected from the group consisting of IWR1, CHIR 99021, PD 0325901, A 83-01, and any combination thereof.

According to certain exemplary embodiments, the expansion medium comprises a combination of the growth factors bFGF, at least one of TGF-β-1, TGF-β-3 and Activin-A, and the small molecule IWR1. According to some embodiments, the expansion medium comprises a combination consisting of the growth factors bFGF, at least one of TGF-β-1, TGF-β-3 and Activin-A, and the small molecule IWR1.

According to further certain exemplary embodiments, the expansion medium comprises a combination consisting of the growth factor bFGF and the small molecule IWR1.

According to certain embodiments, the expansion medium comprises a combination comprising the growth factor bFGF and the small molecules IWR1 and CHIR 99021. According to certain embodiments, the expansion medium comprises a combination consisting of the growth factor bFGF and the small molecules IWR1 and CHIR 99021.

According to additional exemplary embodiments, the expansion medium comprises the growth factor bFGF, and a combination of small molecules consisting of IWR1, CHIR 99021, PD 0325901 and A 83-01.

According to certain embodiments, the expansion medium is further free of animal-derived components.

According to certain embodiments, the non-human-animal is selected from the group consisting of ungulate, poultry, aquatic animals, invertebrate and reptiles. Each possibility represents a separate embodiment of the present invention.

According to certain embodiments, the ungulate is selected from the group consisting of a bovine, an ovine, an equine, a pig, a giraffe, a camel, a deer, a hippopotamus, or a rhinoceros. Each possibility represents a separate embodiment of the present invention.

According to certain exemplary embodiments, the non-human-animal is a bovine. According to some exemplary embodiments, the bovine is of the species *Bos Taurus*.

According to certain embodiments, the PSCs are bovine-derived embryonic stem cells (ESCs).

According to certain exemplary embodiments, the bovine-derived embryonic stem cells are produced by a method comprising the steps of:
(1) obtaining at least one bovine pre-embryo;
(2) culturing the at least one pre-embryo to reach blastocyst or enhanced blastocyst stage;
(3) obtaining at least one cell from the blastocyst; and
(4) culturing the at least one cell in a culture medium comprising a combination of the growth factor bFGF, and at least one of (i) at least one additional growth factor (ii) at least one small molecule selected from the group consisting of an inhibitor of the Wnt-β-catenin signaling pathway, CHIR 99021 (C22H18C12N8), PD 0325901 (C16H14F3IN2O4), and A 83-01 (C25H19N5S), to obtain a plurality of bovine-derived embryonic stem cells.

According to certain embodiments, the at least one bovine pre-embryo is obtained by embryo flushing procedure.

According to certain embodiments, the at least one bovine pre-embryo is a frozen embryo. According to these embodiments, the frozen embryo is thawed before culturing.

It is to be explicitly understood that the at least one PSCs seeded in the expansion medium produced by any method as is known in the art and described hereinabove can be a fresh PSC or can be taken from a frozen stock.

According to certain embodiments, the inhibitor of the Wnt-β-catenin signaling pathway is selected from the group consisting of IWR1, JW67, NSC668036, KY02111, niclosamide, DKK1 or si-Beta-Catenin, porcupine inhibitor, and IWP-2. Each possibility represents a separate embodiment of the present invention.

According to certain exemplary embodiments, the culture medium comprises bFGF and IWR1.

According to certain embodiments, the PSCs are induced PSCs (iPSCs) reprogrammed from non-human-animal cells. According to certain exemplary embodiments, the nonhuman-animal is a mammal. According to further certain exemplary embodiments, the mammal is bovine.

According to other embodiments, the PSCs are non-embryonic stem cells (ESCs).

According to certain exemplary embodiments, the non-genetically modified PSCs are reprogrammed non-human-animal derived cells produced by a method comprising introducing into at least one non-human-animal-derived cell a combination of: (a) at least one reprogramming mRNA encoding reprogramming factor; and (b) at least one double-stranded microRNA; thereby producing at least one iPSC.

According to certain embodiments, the method further comprises introducing into the at least one non-human-animal-derived cell at least one immune evasion mRNA.

According to certain embodiments, the at least one reprogramming mRNA is a synthetically modified mRNA.

According to certain additional exemplary embodiments, the PSCs are reprogrammed non-human-animal-derived cells produced by a method comprising introducing into at least one non-human-animal-derived cell a combination of: (a) at least one reprogramming mRNA encoding reprogramming factor; and (b) at least one inhibitor of at least one microRNA endogenous to the non-human-animal-derived cell; thereby producing at least one iPSC.

According to certain embodiments, the method further comprises introducing into the at least one non-human-animal-derived cell at least one immune evasion mRNA.

According to certain embodiments, the at least one reprogramming mRNA is a synthetically modified mRNA.

According to the teachings of the present invention, the at least one reprogramming mRNA is not integrated into the genome of the cell, thereby the produced iPSCs are not genetically modified.

According to certain embodiments, introducing the at least one reprogramming mRNA, and/or the at least one immune evasion mRNA and/or the at least one double-stranded microRNA and/or the at least one microRNA inhibitor is performed in a serum-free liquid expansion medium.

According to some embodiments, the method further comprises culturing the produced at least one iPSC in the serum-free liquid expansion medium to form a plurality of iPSCs. The serum-free liquid expansion medium is as described hereinabove. According to some embodiments, the serum-free liquid expansion medium used is supplemented with Rock inhibitor.

According to some embodiments, the reprogramming mRNA introduced into the non-human-animal-derived cell or cells encode a reprograming factor selected from the group consisting of OCT4, SOX2, KLF4, cMYC, NANOG, LIN28, KLF5 and any combination thereof. Each possibility represents a separate embodiment of the present invention.

According to yet further embodiments, the double-stranded microRNA is selected from the group consisting of miR-302a, miR-302b, miR-302c, miR-302d, miR-367, miR-218, miR-449b and any combination thereof. Each possibility represents a separate embodiment of the present invention.

According to certain embodiments, the at least one microRNA inhibitor is an RNA inhibitory (RNAi) molecule. According to certain exemplary embodiments, the at least one microRNA inhibitor is targeted to miR-145.

According to certain embodiments, when used, the immune evasion mRNA introduced into the non-human-animal-derived cell or cells is selected from the group consisting of E3, K3, B18R [EKB] from vaccinia virus and any combination thereof. Each possibility represents a separate embodiment of the present invention.

According to certain embodiments, the at least one non-human-animal-derived cell and/or the formed at least one iPSC is incubated at a temperature of between 37.5-39.5° C.

According to certain embodiments, the non-human-animal is of a species selected from the group consisting of ungulate, poultry, aquatic animals, invertebrate and reptiles. Each possibility represents a separate embodiment of the present invention.

According to certain embodiments, the ungulate is selected from the group consisting of a bovine, an ovine, an equine, a pig, a giraffe, a camel, a deer, a hippopotamus, or a rhinoceros.

According to certain exemplary embodiments, the ungulate is a bovine. According to these embodiments, the at least one bovine-derived cell and/or the formed at least one iPSC is incubated at about 38.6° C., the average bovine body temperature.

According to some embodiments, the bovine-derived cells are obtained from bovine umbilical cord, bovine nasopharyngeal mucosa, and bovine milk and blood. According to certain exemplary embodiments, the somatic bovine cells are collected by non-invasive techniques.

According to certain exemplary embodiments, the bovine-derived cells used for producing induced and/or reprogrammed PSCs are obtained from bovine umbilical cord, wherein the cells are selected from the group consisting of endothelial cells, cord lining cells, Wharton's Jelly cells or a combination thereof. According to yet additional embodiments, the bovine-derived cells are obtained from beef cattle breed Belgium Blue. This breed is characterized by a double muscle phenotype due to a natural mutation in the myostatin gene.

According to certain embodiments, the PSCs are encapsulated within a particle. According to certain exemplary embodiments, the particle further comprises the essential agents for the cell proliferation and expansion as described herein. Encapsulation of PSCs within a particle comprising the growth factors and/or small molecules according to the teachings of the present invention may provide for a significant reduction of the production costs, attributed to a smaller amount of these agents that may be required to reach a certain concentration within a particle compared to the amounts required to reach the same concentration in the entire medium volume.

Thus, according to certain embodiments, step (a) of seeding the at least one PSC further comprises encapsulating at least one of said PSCs within a particle and seeding a plurality of the particles within the expansion medium.

According to certain embodiments, the particle comprises an inner core comprising the at least one PSC surrounded by at least one outer shell layer. According to certain embodiments, the outer shell layer is of a fluid-permeable food grade material. According to certain embodiments, the fluid-permeable food grade material is dissolvable. According to these embodiments, the encapsulation is reversible, leading to a release of PSC aggregates formed within the particles upon dissolving of the outer shell layer. According to certain embodiments, the outer shell layer comprises at least one food grade pre-polymer and/or polymer and/or copolymer. According to certain embodiments, the outer shell layer is composed of at least one hydrogel. According to certain embodiments, the hydrogel is a thermos-reversible hydrogel forming the outer shell layer at the temperature of the cell growth. According to certain embodiments, the food grade polymer is selected from the group consisting of alginate, Gellan-Gum, agar, agarose, chitosan, hyaluronic acid, curdlan, carrageenan, pectin, modified starch and combinations thereof. Each possibility represents a separate embodiment of the present invention.

According to certain embodiments, the inner core provides a microenvironment supporting proliferation of the at least one PSC. According to certain embodiments, the inner core microenvironment comprises at least one compound supporting the proliferation of the at least one PSC. According to some embodiments, the at least one agent is formulated in a slow-release and/or sustained release formulation as are known in the art.

According to certain exemplary embodiments, the inner core comprises a combination of the growth factor bFGF, and at least one of (i) at least one additional growth factor; and (ii) at least one small molecule selected from the group consisting of an inhibitor of the Wnt-β-catenin signaling pathway, CHIR 99021 (C22H18C12N8), PD 0325901 (C16H14F3IN2O4), and A 83-01 (C25H19N5S). The combinations of growth factors and/or small molecules are as described hereinabove.

According to certain embodiments, the encapsulated PSCs are proliferating within the inner core to form PSC aggregates within the particle.

According to certain embodiments, the suspension culture is incubated under dynamic rotation, static conditions or a combination thereof.

According to certain exemplary embodiments, the suspension culture is incubated under dynamic rotation conditions.

The present invention now shows that keeping the expansion medium throughout the process at a temperature which is the body temperature of the species from which the cells are derived is of importance for cell proliferation and for obtaining aggregates comprising large number of cells.

According to certain embodiments, incubating is performed at a temperature of between 37.5-39.5° C.

According to certain exemplary embodiments, wherein the non-human-animal is bovine, the incubating temperature is about 38.6° C., the average bovine body temperature.

According to certain embodiments, the volume of the bioreactor is compatible for containing the suspension culture at a volume of from about 50 ml to about 15,000 liters.

According to some embodiments, the volume of the suspension culture is from about 100 ml to about 15,000 liters. According to some embodiments, the volume of the suspension culture is from about 1 liter to about 15,000 liters.

It is an advantage of the method of the present invention that all steps can be performed in a commercial scale volume. According to some embodiments, the volume of the suspension culture is from about 1,000 liters to about 15,000 liters per bioreactor.

According to certain embodiments, the PSC aggregates formed have an average diameter of from about 30 μm to about 500 μm. According to certain embodiments, the PSC aggregates formed have an average diameter of from about 30 μm to about 550 μm. According to certain exemplary embodiments, the PSC aggregates formed have an average diameter of from about 100 μm to about 350 μm.

According to certain embodiments, the aggregates comprise PSCs expressing at least one pluripotency marker. According to certain embodiment, the at least one pluripotency marker is selected from the group consisting of stage-specific embryonic antigen-4 (SSEA4), octamer-binding transcription factor 4 (Oct4), Sall4 transcription factor, Nanog homeobox transcription factor, the translation factor Lin28A, the DNA-methyltransferase Dnmt3b and a combination thereof. Each possibility represents a separate embodiment of the present invention. According to certain exemplary embodiments, the pluripotency marker is SSEA4.

According to additional aspect, the present invention provides homogenous aggregates of non-genetically modified non-human-animal derived PSCs produced according to the methods of the present invention.

According to certain embodiments, the average diameter of the homogenous aggregates is from about 30 μm to about 500 μm. According to certain embodiments, the PSC aggregates formed have an average diameter of from about 30 μm to about 550 μm. According to certain exemplary embodiments, the PSC aggregates formed have an average diameter of from about 100 μm to about 350 μm.

According to another aspect, the present invention provides a suspension comprising serum-free liquid medium and non-human-animal derived cell aggregates, wherein the aggregates comprise at least 70% viable non-genetically modified, non-human-animal derived PSCs.

According to certain embodiments, the non-genetically modified, non-human-animal derived PSCs are dividing every about 16-32 hours.

According to certain embodiments the non-genetically modified non-human-animal-derived PSCs express at least one pluripotency marker.

According to certain embodiments, the pluripotency marker is selected from the group consisting of stage-specific embryonic antigen-4 (SSEA4), octamer-binding transcription factor 4 (Oct4), Sall4 transcription factor, Nanog homeobox transcription factor, the translation factor Lin28A, the DNA-methyltransferase Dnmt3b, and a combination thereof.

According to certain exemplary embodiments, the aggregates within the suspension have an average size of from about 200 μm to about 500 μm.

According to certain exemplary embodiments, the aggregates within the suspension have an average size of from about 200 μm to about 350 μm.

According to certain embodiments, the suspension comprises from about $10^6$ to about $10^9$/ml non-genetically modified, non-human-animal derived PSCs.

According to certain embodiments, the PSCs of the aggregates express at least one surface protein contributing to cell-cell adhesion.

According to certain embodiments, the non-human-animal is selected from the group consisting of ungulate, poultry, aquatic animals, invertebrate and reptiles. Each possibility represents a separate embodiment of the present invention.

According to certain embodiments, the ungulate is selected from the group consisting of a bovine, an ovine, an equine, a pig, a giraffe, a camel, a deer, a hippopotamus, and a rhinoceros. Each possibility represents a separate embodiment of the present invention.

According to certain exemplary embodiments, the non-human-animal is a bovine. According to some exemplary embodiments, the bovine is of the species *Bos Taurus*.

The PSCs aggregates of the present invention may be used per se, for example as experimental and research tool or a starting material for further uses.

According to certain embodiments, the PSCs aggregates of the present invention may be used as a staring material in the industry of cell-grown meat. According to these embodiments, the PSCs are further differentiated to at least one of adipocyte cells, muscle cells, stromal cell, and endothelial lineages.

According to yet further aspect, the present invention provides cell grown meat culture comprising homogenous aggregates of non-genetically modified non-human-animal-derived PSCs or a suspension comprising same according to the teachings of present invention.

According to yet additional aspect, the present invention provides a cell grown meat product comprising a progeny of the homogenous aggregates of non-genetically modified non-human-animal-derived PSCs of the present invention. According to certain embodiments, the progeny comprises cells differentiated from the PSCs to form at least one of muscle cells, stromal cell, endothelial cells and adipocytes.

According to yet further aspect, the present invention provides a method for differentiating non-human-animal cells selected from the group consisting of PSCs, offspring thereof, somatic cells and combinations thereof to adipocyte cells, the method comprising incubating the cells in a serum-free liquid medium comprising at least one of (i) at least one inhibitor of the Wnt-β-catenin signaling pathway; and (ii) at least one type of fatty acid; thereby differentiating said cells to adipocyte cells.

According to certain embodiments, the medium comprises a combination of at least one inhibitor of the Wnt-β-catenin signaling pathway and at least one type of fatty acid.

According to certain embodiments, the medium further comprises the growth factor bFGF. According to certain embodiments, the medium further comprises a Rock inhibitor.

According to certain embodiments, incubating the cells is for at least 4 days.

According to certain embodiments, the inhibitor of the Wnt-β-catenin signaling pathway is selected from the group consisting of IWR1, JW67, NSC668036, KY02111, niclosamide, DKK1 or si-Beta-Catenin, porcupine inhibitor, and IWP-2.

According to certain exemplary embodiments, the at least one inhibitor of the Wnt-β-catenin signaling pathway is IWR-1.

According to certain embodiments, the fatty acid is selected from the group consisting of free fatty acid, low molecular weight fatty acid, esters thereof, salts thereof and any combination of same.

According to certain embodiments, the PSC are selected from the group consisting of induced PSCs (iPSC) and embryonic stem cells.

According to certain embodiments the PSCs derivatives are stromal stem cells isolated from fat tissue.

According to certain embodiments, the cells comprise a population of cells derived from embryonic muscle tissue. According to certain embodiments, the population of cells derived from embryonic muscle tissue comprises embryonic fibroblasts (EFs).

According to certain embodiments, the cells to be differentiated are derived from a non-human-animal selected from the group consisting of ungulate, poultry, aquatic animals, invertebrate and reptiles. Each possibility represents a separate embodiment of the present invention.

According to certain embodiments, the ungulate is selected from the group consisting of a bovine, an ovine, an equine, a pig, a giraffe, a camel, a deer, a hippopotamus, or a rhinoceros. Each possibility represents a separate embodiment of the present invention.

According to certain exemplary embodiments, the non-human-animal is a bovine.

It is to be understood that any combination of each of the aspects and the embodiments disclosed herein is explicitly encompassed within the disclosure of the present invention.

Other objects, features and advantages of the present invention will become clear from the following description.

BRIEF DESCRIPTION OF THE DRAWINGS

FIGS. 1A-1B shows embryonic stem cells derived from flushed bovine embryos (bESCs). FIG. 1A is shows representative morphology of pre-embryo isolated from the *Zona Pellucida* and attached for feeder layer 1 day after seeding. FIG. 1B shows that 5 days after seeding a migration of cells with ESC-like morphology is seen.

FIG. 2 shows proliferation of bESC in serum-free medium mTeSR1® supplemented with 2.5 µM IWR1, on inactivated mouse embryonic fibroblasts (iMEFs) as a feeder layer.

FIG. 3A shows percentage of positive staining of Alp 0501 (17 experiments) and Alp 0505 (5 experiments) with SSEA4 antibody by Flow cytometry. FIG. 3B shows expression of pluripotency markers relative to the expression in BEF measured by Real-time PCR.

FIG. 4A: PSC line Alp 0501. FIG. 4B: PSC line Alp 0505.

FIG. 6A; one-day post seeding in suspension. FIG. 6B: two-days post seeding in suspension. FIG. 6C: seven-days post seeding in suspension. Representative images, scale bar=200 µm.

FIG. 9A shows 3 days old aggregates serving as a source material for dis-aggregation. FIG. 9B shows aggregates formed from small aggregates/single cells obtained from the aggregates of FIG. 9A re-seeded in a medium including dissociation reagent. Representative images, scale bar=650 µm.

FIG. 10A; Umbilical Cord (UC); FIG. 10B: Wharton's Jelly; FIG. 10C: Tissue cuts; FIG. 10D: Isolated UC cells.

FIG. 12A: Embryonic stem cell (ES)-like colonies 2 weeks following transfection. FIG. 12B: bright-field image showing bovine ES-like colony morphology following adaptation to vitronectin coated surface. FIG. 12C: Episomal CoMiP plasmid did not integrate into the bovine host genome.

FIG. 13C: qPCR analysis of bovine OCT4 transcript in untreated BEF cells, iBEF cells (BEF cells transfected with modified mRNAs encoding bovine OSKM for inducing reprogramming) and human iPSCs cells. Values are compared to untreated BEF cells (RQ=1) and normalized to bovine beta-actin.

DETAILED DESCRIPTION OF THE INVENTION

Figure 3A:
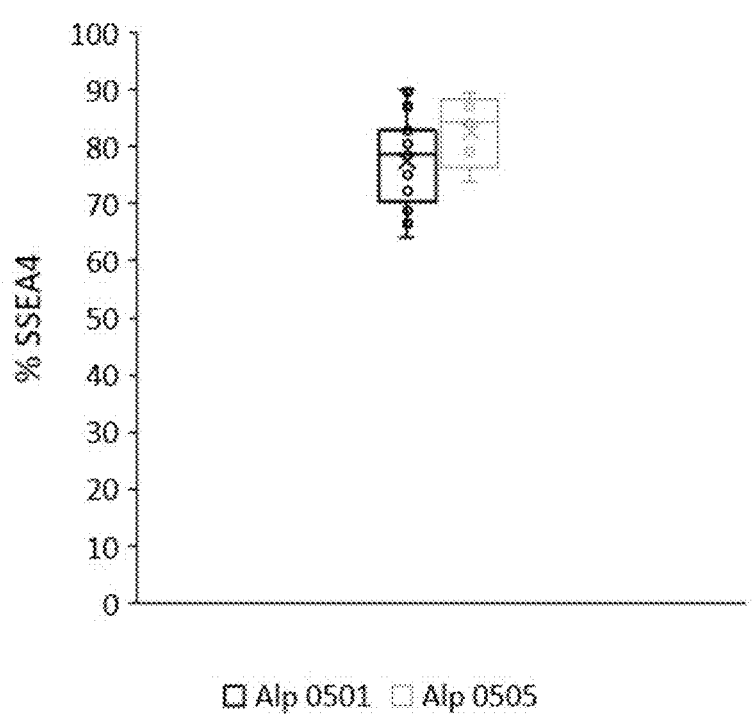
FIGS. 3A-3B demonstrates the pluripotency of the proliferated bESCs.

The present invention provides methods for forming homogenous 3D aggregates at a commercial scale from non-human-animal-derived PSCs suspended in liquid serum-free medium comprising specific combinations of growth factors and small molecules added to the medium, and devoid of cell-adhering surface.

The present invention fulfills a long-felt need for producing non-GM cell grown meat for food consumption from PSCs derived from non-human-animals, particularly bovine, under large-scale conditions.

Definitions

The terms "comprise", "comprising", "includes", "including", "having" and their conjugates mean "including but not limited to".

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible sub ranges as well as individual numerical values within that range. For example, description of a range such as from 1 to 6 should be considered to have specifically disclosed sub ranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

The term "about" as used herein refers to a variation of a numerical designation of +10% or −10% of the numerical designation.

The terms "animal" and "non-human animal" with reference to cells derived therefrom are used herein interchangeably and refers only to cells of non-human-animals.

As used herein the term "pluripotent stem cells (PSCs)" refers to cells that can propagate indefinitely, as well as give rise to every other cell type in the body.

As used herein the term "induced pluripotent stem cells (iPSCs)" refers to a type of pluripotent stem cell that can be generated directly from somatic cells.

As used herein the term "embryonic stem cells (ESC)" refers to a type of pluripotent stem cell derived from non-human-animal, particularly bovine blastocyst.

The term "3 dimensional (3D)" refers to a cell culture of cells grown in a liquid suspension and do not adhere to a solid and/or semi-solid surface. A 3D cell culture is an artificially created environment in which biological cells are permitted to grow or interact with their surrounding cells. 3D cell culture allows in vitro growth of cells in all directions, similar to how they would grow in vivo.

The term "non-genetically modified (non-GM)" refers to intact cells, with no genome alteration/no foreign nucleic acid integration into the genome due to transfection with foreign nucleic acids.

The term "aggregates" as used herein refers to the phenomenon by which dissociated cells intermixed in vitro tend to group themselves with other cells also referred to a "floating aggregates".

As used herein, the term "homogenous" with regard to the aggregates of the present invention refers to a plurality of aggregates comprising at least 70% non-human-animal-derived PSCs and having average diameter of from about 30 µm to about 500 µm. According to certain embodiments, the aggregate average diameter is from about 30 µm to about 450 µm, from about 30 µm to about 400 µm or from about 30 µm to about 350 µm. According to some embodiments, the aggregate average diameter is above 300 µm. According to certain exemplary embodiments, the aggregate average diameter is from about 30 µm to about 350 µm. According to certain embodiments, a final suspension product comprises aggregates having an average diameter of from about 250 µm to about 350 µm.

As used herein, the term "serum-free" with regard to a medium refers to a medium with no animal sera.

As used herein, the term "animal-derived component-free" with regard to a medium refers to a medium not containing any component of animal origin, particularly to a medium not containing mammal-derived components.

The term "cell grown meat" is used herein to describe meat grown from in vitro animal cell culture distinguished from meat of slaughtered animals. Additional terms that may be used in the Art to describe meat grown from in vitro animal cell culture include cultured meat, cultivated meat, clean meat, lab-grown meat, test tube meat, in vitro meat, tube steak, synthetic meat, cell-cultured meat, cell grown meat, tissue engineered meat, engineered meat, artificial meat, and manmade meat.

As used herein, the term "closed system" with reference to cell cultivation system refers to a system comprising all the elements required to complete a growth cycles of PSCs aggregates according to the teachings of the present invention.

The term "reprogramming" refers to conversion of one specific cell type to another. According to certain embodiments of the present invention, reprogramming is the conversion of a somatic cell type, to a pluripotent cell type known as an induced pluripotent stem cell, or iPSC.

The term "reprogramming mRNAs" as used herein refers to the mRNAs encoding any one of the following transcription factors: OCT4, SOX2, KLF4, cMYC, NANOG, LIN28 and KLF5.

The terms "vessel" or "tissue culture vessel" are used herein interchangeably and refer to any receptacle in which the PSCs can grow in suspension without adhering to the receptacle material. The receptacle can be of a variety of sizes, from the range of milliliters (e.g. non-adherent plate or Erlenmeyer flask) to the range of thousands of liters (e.g. bioreactor).

According to one aspect, the present invention provides a method of producing aggregates of non-genetically modified non-human-animal-derived PSCs comprising the steps of: (a) seeding at least one PSCs in an expansion medium, the expansion medium is a serum-free liquid medium comprising the growth factor bFGF, at least one additional growth factor and/or at least one small molecule selected from the group consisting of an inhibitor of the Wnt-β-catenin signaling pathway, CHIR 99021 ($C_{22}H_{18}Cl_2N_8$), PD 0325901 ($C_{16}H_{14}F_3IN_2O_4$), A 83-01 ($C_{25}H_{19}N_5S$), and any combination thereof to form a suspension culture; and (b) growing the suspension culture under conditions enabling aggregate formation and aggregate expansion, thereby forming homogenous aggregates of said PSCs. Each possibility represents a separate embodiment of the present invention.

According to certain embodiments, the seeding and growing is within a vessel having walls of a material to which the PSCs and/or aggregates comprising same do not adhere.

According to certain embodiments, the expansion medium is further free of animal-derived components.

bFGF (Basic fibroblast growth factor, also known as FGF2) possess a broad mitogenic and cell survival activities, and is involved in a variety of biological processes, including embryonic development, cell growth, morphogenesis, tissue repair, tumor growth and invasion. bFGF activates JAK/STAT, PI3K, ERK1/2, and other receptor tyrosine kinase (RTK) signaling pathways. It supports the maintenance of undifferentiated human embryonic stem cells.

According to certain embodiments, the expansion medium comprises a combination consisting of bFGF and at least one additional growth factor. According to certain exemplary embodiments, the additional growth factor is a protein of the family of transforming growth factor beta (TGF-β, also symbolled as TGFB).

TGF-β is a multifunctional cytokine belonging to the transforming growth factor superfamily that includes three different mammalian isoforms (TGF-β1 to 3, or TGFB1, TGFB2, TGFB3) and many other signaling proteins, including Activin-A. Activated TGF-β complexes with other factors to form a serine/threonine kinase complex that binds to TGF-β receptors. TGF-β receptors are composed of both type 1 and type 2 receptor subunits. After the binding of TGF-β, the type 2 receptor kinase phosphorylates and activates the type 1 receptor kinase that activates a signaling cascade. This leads to the activation of different downstream substrates and regulatory proteins, inducing transcription of different target genes that function in differentiation, chemotaxis, proliferation, and activation of many immune cells.

According to certain embodiments, the expansion medium comprises a combination consisting of bFGF and at least one small molecule.

WNT-β-catenin signaling is involved in a multitude of developmental processes and the maintenance of adult tissue homeostasis by regulating cell proliferation, differentiation, migration, genetic stability and apoptosis, and known inhibitors as well as future inhibitors to be developed of this pathway can be used according to the teachings of the present invention. Known inhibitors are listed, for example, in Kahn M. 2014. Nat Rev Drug Discov. 13(7):513-32. doi: 10.1038/nrd4233.

According to certain embodiments, the inhibitor of the Wnt-β-catenin signaling pathway is selected from the group consisting of IWR1, JW67, NSC668036, KY02111, niclosamide, DKK1 or si-Beta-Catenin, porcupine inhibitor, and IWP-2. Each possibility represents a separate embodiment of the present invention.

According to certain exemplary embodiments, the inhibitor of the Wnt-β-catenin signaling pathway is IWR1. IWR1 potently inhibits WNT signaling by blocking a cell-based WNT/β-catenin pathway. It has been shown to promote self-renewal and maintain pluripotency of human embryonic stem cells and mouse Epi-stem cells when used in combination with CHIR 99021 (Kim et al., Nat Commun. 2013, 4: 2403). It has also been shown that a culture medium comprising the combination of IWR1 and bFGF supports growth and maintenance of pluripotent embryonic stem cells from bovine blastocytes (Bogliotii Y S et al., ibid). According to certain embodiments, the IWR1 concentration in the medium is from about 1 µM to about 10 µM. According to some embodiments, the IWR1 concentration in the medium is from about 2 µM to about 10 µM.

CHIR 99021 (6-[[2-[[4-(2,4-Dichlorophenyl)-5-(5-methyl-1H-imidazol-2-yl)-2-pyrimidinyl]amino]ethyl]amino]-3-pyridinecarbonitrile) is an aminopyrimidine derivate that is a selective and potent inhibitor of glycogen synthase kinase 3 (GSK-3).

PD0325901 (N-[(2R)-2,3-Dihydroxypropoxy]-3,4-difluoro-2-[(2-fluoro-4-iodophenyl)amino]-benzamide is a potent and selective MEK1 and MEK2 inhibitor.

PD 0325901 can be used with CHIR 99021 to reprogram somatic cells into iPSCs and promote cell self-renewal.

A83-01 (3-(6-Methyl-2-pyridinyl)-N-phenyl-4-(4-quinolinyl)-1H-pyrazole-1-carbothioamide) is a potent inhibitor of TGF-β type I receptor ALK5 kinase, type I activin/nodal receptor ALK4 and type I nodal receptor ALK7 (IC50 values are 12, 45 and 7.5 nM respectively). A83-01 blocks phosphorylation of Smad2 and inhibits TGF-β-induced epithelial-to-mesenchymal transition. A83-01 is used to inhibit differentiation in iPSCs and maintain in vitro cellular self-renewal.

According to other embodiments, the expansion medium comprises the two growth factors bFGF and TGF-β and at least two small molecules selected from the group consisting of IWR1, CHIR 99021 ($C_{22}H_{18}Cl_{12}N_8$), PD 0325901 ($C_{16}H_{14}F_3IN_2O_4$), and A 83-01 ($C_{25}H_{19}N_5S$).

According to certain embodiments, the expansion medium comprises a combination of the growth factor bFGF, and at least one small molecule selected from the group consisting of IWR1, CHIR 99021, PD 0325901, A 83-01, and any combination thereof. According to some embodiments, the expansion medium comprises a combination consisting of the growth factor bFGF, and the small molecule IWR1.

According to certain exemplary embodiments, the expansion medium comprises a combination of the growth factors bFGF and at least one of TGF-β-1, TGF-β-3, and Activin-A and the small molecule IWR1. According to some embodiments, the expansion medium comprises a combination consisting of the growth factors bFGF, at least one of TGF-β-1, TGF-β-3, and Activin A and the small molecule IWR1.

According to certain embodiments, the expansion medium comprises a combination comprising the growth factor bFGF and the small molecules IWR1 and CHIR 99021. According to certain embodiments, the expansion medium comprises a combination consisting of the growth factor bFGF and the small molecules IWR1 and CHIR 99021.

According to certain exemplary embodiments, the expansion medium comprises a combination consisting of the growth factors bFGF and the small molecule A 83-01. According to further exemplary embodiments, the expansion medium comprises the combination of the growth factors bFGF, at least one of TGF-β-1, TGF-β-3, and Activin-A, and a combination of small molecules consisting of CHIR 99021, PD 0325901 and A 83-01.

Any non-human-animal-derived pluripotent stem cells as are known in the art can be used according to the teachings of the present invention. According to certain embodiments, the non-human-animal is of a species selected from the group consisting of ungulate, poultry, aquatic animals, invertebrate and reptiles. Each possibility represents a separate embodiment of the present invention.

According to certain embodiments, the ungulate is selected from the group consisting of a bovine, an ovine, an equine, a pig, a giraffe, a camel, a deer, a hippopotamus, or a rhinoceros. According to some embodiments the ungulate is a bovine. According to certain exemplary embodiments, the bovine is a cow.

Commercial preparations of, for example, bovine-derived PSCs are also available, including blastocyst-derived PSCs.

According to some embodiments, the PSCs are embryonic stem cells (ESCs).

According to some embodiments, the PSCs are non-embryonic stem cells (ESCs).

According to certain embodiments, the PSCs are induced PSCs (iPSCs) reprogrammed from somatic cells.

According to certain embodiments, the PSCs are induced PSCs (iPSCs) reprogrammed from somatic cells not including ESCs.

The reprogramming of the cells to produce iPSCs can be performed by any method known in the art, including, for example, the method described in Peleganove et al. (Poleganov et al., Hum. Gene Ther. 2015; 26:751-766).

According to certain exemplary embodiments, the method of producing the aggregates of non-genetically modified non-human-animal-derived PSCs comprises the steps of:
  (a) seeding the at least one PSC in the expansion medium to form seeding suspension culture;
  (b) incubating the seeding suspension culture to form PSC aggregates;
  (c) disaggregating the aggregates into smaller aggregates and/or single cells;
  (d) repeating steps (a)-(c) at least once to obtain a desired PSC concentration; and
  (e) expanding the PSCs by repeating steps (a)-(b) as to obtain a desired aggregate concentration.

According to certain exemplary embodiments, disaggregating the aggregates comprises exposing said aggregates to a dissociation reagent and/or to a dissociation force. According to some embodiments, the dissociation reagent comprises at least one proteolytic enzyme and optionally at least one DNA degrading enzyme and/or chelating agent. According to some embodiments, the dissociation reagent comprises at least one proteolytic enzyme, at least one DNA degrading enzyme and a chelating agent. According to certain embodiments, the chelating agent is selected from EDTA and EGTA. According to some exemplary embodiments, the proteolytic enzyme is trypsin.

According to some embodiments, the dissociation force is a shear force. According to certain embodiments, the shear force rate is set by an impeller embedded within the vessel.

According to certain embodiments, the step of disaggregating further comprises washing the homogenous aggregates prior to exposing said aggregates to the dissociation reagent and/or dissociation force with an aqueous-based washing medium.

According to certain embodiments, steps (a)-(c) are repeated at least twice, at least 3 times, at least 4 times, at least 5 times and more. It is to be explicitly understood that the number of repeats may be indefinite and would depend on the amount of PSCs required for the intended use. According to certain embodiments, the steps of aggregation and disaggregation are repeated until a cell concentration of at least $10^6$ cells/ml is reached. According to some embodiments, the steps of aggregation and disaggregation are repeated until a cell concentration of at least $5\times10^6$ cells/ml, at least $10^7$ cells/ml, at least $5\times10^7$ cells/ml, at least $10^8$ cells/ml, at least $5\times10^8$ cells/ml, or at least $10^9$ cells/ml or more is reached.

According to certain embodiments, steps (a)-(c) are repeated in the same medium. According to some embodiments, the medium comprises dissociation reagent.

According to certain embodiments, the seeding is within a non-adherent tissue culture vessel.

According to certain embodiments, step (a) of seeding the at least one PSC further comprises adding an inhibitor of Rho-associated protein kinase (Rock).

Any ROCK inhibitor currently known in the Art or to be developed in the future can be used according to the teachings of the present invention. According to certain embodiments, the Rock inhibitor is selected from the group consisting of Thiazovivin, Fasudil, Ripasudil, Netarsudil, RKI-1447, Y-27632, GSK429286A, Y30141. Each possibility represents a separate embodiment of the present invention. According to certain exemplary embodiments, the Rock inhibitor is Y-27632 dihydrochloride (1R,4r)-4-((R)-1-aminoethyl)-N-(pyridin-4-yl)cyclohexanecarboxamide).

According to certain embodiments, step (a) of seeding the at least one PSC further comprises encapsulating at least one non-genetically modified non-human-animal-derived PSC within a particle and seeding a plurality of the particles within the expansion medium.

According to certain embodiments, the particle comprises an inner core surrounded by at least one outer shell layer, wherein the inner core further comprises at least one compound supporting proliferation of the at least one non-genetically modified non-human-animal-derived PSC. According to certain embodiments, the outer shell layer is of a food grade fluid permeable material. According to certain embodiment, the outer shell layer is designed for reversible encapsulation, such that upon exposing the particle to certain conditions the PSCs aggregates formed within the capsule are released. According to certain embodiments, fluid-permeable food grade material of the outer shell layer is dissolvable. It is to be explicitly understood that the inner core microenvironment of the particle provides free space enabling the initial cell-cell interactions and subsequent cell growth, but no cell agglomeration and hydrodynamic stresses. Accordingly, the particle encapsulating the PSCs could significantly improve the culture efficiency and aggregate formation.

According to certain embodiments, the outer shell layer comprises at least one food grade polymer or a co-polymer. According to certain embodiments, the outer shell layer comprises one or more polymers forming a hydrogel. According to certain embodiments, the hydrogel is a thermos-sensitive and/or thermo-reversible hydrogel. Suitable polymers and hydrogel materials are known in the art. For example, alginate is a polymer well known to be used for encapsulation. Gellan-Gum forms a hydrogel at low temperatures (gels at body temperature) when blended with monovalent or divalent cations. Chitosan forms a firm ionotropic hydrogel with phosphate ions. Curdlan can form low-set gel (thermo-reversible) and high-set gel (thermo-irreversible) mainly based on different heating temperatures. Agarose, hyaluronic acid, carrageenan, modified starches and pectin—all are known to be suitable for forming an outer shell layer according to the teachings of the present invention.

According to certain embodiments, the at least one compound supporting proliferation present within the inner core microenvironment is formulated in a slow-release and/or sustained release formulation as are known in the art.

According to certain embodiments, the tissue culture vessel is made of a material to which the PSCs do not adhere. Thus, the PSCs and/or aggregates comprising same are free within a suspension and are not adhered to any surface.

According to certain embodiments, the suspension culture is grown as to reach a desired pluripotent cell concentration of from about 100,000 cells/ml to about 50,000,000 cells/ml. According to certain embodiments, the suspension culture is grown as to reach PSCs at a concentration of from about 300,000 cells/ml to about 10,000,000 cells/ml or to about 1,000,000 cells/ml.

According to certain embodiments, the suspension culture is incubated under dynamic rotation, static condition, or a combination thereof.

According to certain exemplary embodiments, the suspension culture is incubated under dynamic rotation conditions.

According to certain embodiments, incubating is performed at the body temperature of the animal from which the cells were derived.

According to certain embodiments, incubating is performed at a temperature of between 37.5-39.5° C.

According to certain exemplary embodiments, when the non-human animal is a bovine, the incubating temperature is about 38.6° C., the average bovine body temperature.

According to certain embodiments, the volume of the suspension culture is from about 100 ml to about 15,000 liters per vessel.

According to some embodiments, the volume of the suspension culture is from about 500 ml to about 15,000 liters per vessel. According to some embodiments, the volume of the suspension culture is from about 1 liter to about 15,000 liters per vessel. According to some embodiments, the volume of the suspension culture is from about 1 liter to about 1,500 liters per vessel. According to some embodiments, the volume of the suspension culture is from about 1 liter to about 150 liters per vessel.

It is an advantage of the method of the present invention that all steps can be performed in a commercial scale volume, and in a closed system. According to some embodiments, the volume of the suspension culture is from about 1,000 liters to about 15,000 liters per vessel.

According to certain embodiments, the PSC aggregates formed have an average diameter of from about 30 μm to about 500 μm. According to some embodiments, the aggregates have an average diameter of from about 100 μm to about 500 μm. According to some embodiments, the aggregates have an average diameter of from about 150 μm to about 500 μm. According to certain exemplary embodiments, the aggregates have an average diameter of from about 300 μm to 550 μm. According to certain exemplary embodiments, the aggregate average diameter is from about 30 μm to about 350 μm. According to certain exemplary embodiments, the aggregate average diameter is from about 250 μm to about 350 μm.

According to certain exemplary embodiments, the PSCs are reprogrammed non-human-animal derived cells produced by a method comprising introducing into at least one non-human-animal-derived cell a combination of: (a) at least one reprogramming mRNA encoding a reprogramming factor; and (b) at least one double-stranded microRNA; thereby producing at least one iPSC.

According to certain embodiments, the method further comprises introducing into the at least one non-human-animal-derived cell at least one immune evasion mRNA.

According to certain embodiments, the at least one reprogramming mRNA is a synthetically modified mRNA.

According to certain additional exemplary embodiments, the PSCs are reprogrammed non-human-animal-derived cells produced by a method comprising introducing into at least one non-human-animal-derived cell a combination of: (a) at least one reprogramming mRNA; and (b) at least one inhibitor of at least one microRNA endogenous to the non-human-animal derived cell; thereby producing at least one iPSC.

According to certain embodiments, the method further comprises introducing into the at least one non-human-animal-derived cell at least one immune evasion mRNA.

According to certain embodiments, the at least one reprogramming mRNA encoding a reprograming factor and/or the at least one double-stranded microRNA are of human or non-human-animal origin.

According to certain embodiments, the non-human-animal is a bovine. According to these embodiments, the at least one reprogramming mRNA encoding a reprograming factor and/or the at least one double-stranded microRNA are of human or bovine origin.

Introducing the oligo- or polynucleotides of the invention into PSCs can be performed by any method as is known in the art.

According to the teachings of the present invention, the at least one mRNA is not integrated into the genome of the cell, thereby the produced iPSCs are not genetically modified.

According to certain embodiments, introducing the at least one reprogramming mRNA, and/or the at least one immune evasion mRNA and/or the at least one double-stranded microRNA and/or the at least one microRNA inhibitor is performed in a serum-free, animal-derived component-free liquid expansion medium. According to some embodiments, the medium is further animal-derived component free.

According to some embodiments, the method further comprises culturing the produced at least one iPSC in the serum-free liquid expansion medium to form a plurality of iPSCs. The serum-free liquid expansion medium is as described hereinabove. According to some embodiments, the serum-free liquid expansion medium used is supplemented with Rock inhibitor.

According to some embodiments, the reprogramming mRNA introduced into the non-human-animal-derived cell or cells is selected from the group consisting of OCT4, SOX2, KLF4, cMYC, NANOG, LIN28, KLF5 and any combination thereof. Each possibility represents a separate embodiment of the present invention.

According to further embodiments, the immune evasion mRNA introduced into the non-human-animal-derived cell or cells is selected from the group consisting of E3, K3, B18R [EKB] from vaccinia virus and any combination thereof. Each possibility represents a separate embodiment of the present invention.

According to yet further embodiments, the double-stranded microRNA is selected from the group consisting of miR-302a, miR-302b, miR-302c, miR-302d, miR-367, miR-218, miR-449b and any combination thereof. Each possibility represents a separate embodiment of the present invention.

According to certain embodiments, the at least one microRNA inhibitor is an RNA inhibitory (RNAi) molecule. According to certain exemplary embodiments, the at least one microRNA inhibitor is targeted to miR-145.

According to certain embodiments, when used, the immune evasion mRNA introduced into the non-human-animal-derived cell or cells is selected from the group consisting of E3, K3, B18R [EKB] from vaccinia virus and any combination thereof. Each possibility represents a separate embodiment of the present invention.

According to certain embodiments, the at least one non-human-animal-derived cell and/or the formed at least one iPSC is incubated at a temperature of between 37.5-39.5° C.

According to certain embodiments, the non-human-animal is of a species selected from the group consisting of ungulate, poultry, aquatic animals, invertebrate and reptiles. Each possibility represents a separate embodiment of the present invention.

According to certain embodiments, the ungulate is selected from the group consisting of a bovine, an ovine, an equine, a pig, a giraffe, a camel, a deer, a hippopotamus, or a rhinoceros.

According to certain exemplary embodiments, the ungulate is a bovine. According to these embodiments, the at least one bovine-derived cell and/or the formed at least one iPSC is incubated at 38.6° C., the average bovine body temperature.

According to some embodiments, the bovine-derived cells are obtained from bovine umbilical cord, bovine nasopharyngeal mucosa, and bovine blood. According to certain exemplary embodiments, the somatic bovine cells are collected by non-invasive techniques.

According to certain exemplary embodiments, the bovine-derived cells are obtained from bovine umbilical cord, wherein the cells are selected from the group consisting of endothelial cells, cord lining cells, Wharton's Jelly cells or a combination thereof. According to yet additional embodiments, the bovine-derived cells are obtained from beef cattle breed Belgium Blue. This breed is characterized by a double muscle phenotype due to a natural mutation in the myostatin gene.

According to additional aspect, the present invention provides homogenous aggregates of non-genetically modified non-human-animal-derived PSCs produced according to the methods of the present invention. According to certain embodiments, the aggregates comprise at least 70% viable cells expressing at least one pluripotency marker. According to certain embodiments, the pluripotency marker is selected from the group consisting of SSEA4, Oct4, Nanog, Lin28A, Sall4, Dnmt3b and a combination thereof. According to certain exemplary embodiments, the pluripotency marker is SSEA4.

According to another aspect, the present invention provides a suspension comprising serum-free liquid medium and non-human-animal-derived cell aggregates comprising at least 70% viable PSCs expressing at least one pluripotency marker. According to certain embodiments, the PSCs are dividing every about 16-32 hours. According to certain embodiments, the PSCs are dividing every about 16-24 hours.

According to certain embodiments, the PSCs of the aggregates express at least one surface protein contributing to cell-cell adhesion.

According to yet further aspect, the present invention provides cell grown meat culture comprising the homogenous aggregates of non-genetically modified non-human-animal derived PSCs or a suspension comprising same according to the present invention.

According to yet additional aspect, the present invention provides a cell grown meat product comprising a progeny of the homogenous aggregates of non-genetically modified non-human-animal-derived PSCs of the present invention.

The non-human animal is as described hereinabove. According to certain exemplary embodiments, the non-human-animal is bovine.

According to certain embodiments, the progeny comprises cells differentiated from the PSCs to form at least one of muscle cells, stromal cell, endothelial cells and adipocytes.

The present invention now shows that, unexpectedly, the presence of fatty acids within expansion medium according to certain embodiments of the present invention leads to differentiation of bovine derived PSCs or culture of BEFs to adipocytes.

According to yet further aspect, the present invention provides a method for differentiating non-human-animal cells selected from the group consisting of PSCs, offspring thereof, somatic cells and combinations thereof to adipocyte cells, the method comprising incubating the cells in a serum-free liquid medium comprising at least one of (i) at least one inhibitor of the Wnt-β-catenin signaling pathway; and (ii) at least one type of fatty acid; thereby differentiating said cells to adipocyte cells.

According to certain embodiments, the medium comprises a combination of at least one inhibitor of the Wnt-β-catenin signaling pathway and at least one type of fatty acid.

According to certain embodiments, the medium further comprises the growth factor bFGF.

According to certain embodiments, the medium further comprises Rock inhibitor.

According to certain embodiments, incubating the cells is for at least 4 days. According to other embodiments, incubating the cells is for at least 5 days, at least 6 days, at least 7 days, at least 8 days, at least 9 days or at least 10 days and more. Each possibility represents a separate embodiment of the present invention.

According to certain embodiments, the inhibitor of the Wnt-β-catenin signaling pathway is selected from the group consisting of IWR1, JW67, NSC668036, KY02111, niclosamide, DKK1 or si-Beta-Catenin, porcupine inhibitor, and IWP-2.

According to certain exemplary embodiments, the at least one inhibitor of the Wnt-β-3-catenin signaling pathway is IWR-1.

According to certain embodiments, the fatty acid is selected from the group consisting of free fatty acid, low molecular weight fatty acid, esters thereof, salts thereof and any combination of same.

According to certain embodiments the PSCs comprise stromal stem cells isolated from fat tissue.

According to certain embodiments, the cells comprise a population of cells derived from embryonic muscle tissue. According to some embodiments, the cells derived from embryonic muscle tissue comprise embryonic fibroblasts (EFs).

The non-human-animal is as described hereinabove.

Food products comprising the cell grown meat of the present invention are also encompassed within the scope of the present invention.

According to another aspect, the present invention provides an expansion medium for expending non-human-animal-derived PSCs comprising a combination of the growth factor bFGF and at least one of (i) at least one additional growth factor and (ii) at least one small molecule selected from the group consisting of an inhibitor of the Wnt-β-catenin signaling pathway, CHIR 99021, PD 0325901 and A 83-01 or any combination thereof, wherein the expansion medium is serum-free and is devoid of inactivated feeder cells. According to certain embodiments, the expansion medium is further devoid of organic matrix. According to certain embodiments, the expansion medium is further animal-derived component free.

According to certain embodiments, the expansion medium is capable of maintaining non-human-mammalian pluripotent stem cells in a pluripotent state when cultured in a suspension culture devoid of substrate adherence.

According to certain embodiments, the expansion medium is devoid of a proteinase inhibitor.

According to certain embodiments, the expansion medium comprises a combination consisting of bFGF and at least one additional growth factor. According to certain exemplary embodiments, the additional growth factor is a protein of the TGF-β-superfamily. According to certain exemplary embodiments, the TGF-β is selected from the group consisting of TGF-β-1, TGF-β-3, Activin-A and any combination thereof.

According to certain embodiments, the expansion medium comprises a combination consisting of bFGF and at least one small molecule.

According to certain embodiments, the inhibitor of the Wnt-β-catenin signaling pathway is selected from the group consisting of IWR1, JW67, NSC668036, KY02111, niclosamide, DKK1 or si-Beta-Catenin, porcupine inhibitor, and IWP-2.

According to certain exemplary embodiments, the inhibitor of the Wnt-β-catenin signaling pathway is IWR1.

According to certain exemplary embodiments, the expansion medium comprises a combination of the growth factors bFGF, at least one of TGF-β-1, TGF-β-3 and Activin-A, and a small molecule selected from the group consisting of IWR1, CHIR 99021, PD 0325901, A 83-01 and any combination thereof.

According to certain exemplary embodiments, the expansion medium comprises a combination of the growth factors bFGF, at least one of TGF-β-1, TGF-β-3, and Activin-A, and the small molecule IWR1. According to some embodiments, the expansion medium comprises a combination consisting of the growth factors bFGF and at least one of TGF-β-1, TGF-β-1 and Activin A, and the small molecule IWR1.

According to certain embodiments, the expansion medium comprises a combination comprising the growth factor bFGF, and the small molecules IWR1 and CHIR 99021. According to certain embodiments, the expansion medium comprises a combination consisting of the growth factor bFGF and the small molecules IWR1 and CHIR 99021.

According to further certain exemplary embodiments, the expansion medium comprises a combination consisting of the growth factor bFGF and the small molecules IWR1.

According to another aspect, the present invention provides a kit for expanding non-human-animal-derived PSCs aggregates comprising serum-free growth medium devoid of inactivated feeder layer cells; the growth factor bFGF; at least one of an additional growth factor; and at least one small molecule selected from the group consisting of an inhibitor of the Wnt-β-catenin signaling pathway, CHIR 99021, PD 0325901 and A 83-01. According to certain embodiments, the kit further comprises instructions for growing conditions for expanding non-human-animal-derived PSCs aggregates.

According to certain embodiment the serum-free medium is further devoid of organic matrix. According to certain embodiments, the expansion medium is further animal-derived-component free.

According to certain embodiments, the inhibitor of the Wnt-β-catenin signaling pathway is selected from the group consisting of IWR1, JW67, NSC668036, KY02111, niclosamide, DKK1 or si-Beta-Catenin, porcupine inhibitor, and IWP-2.

According to certain exemplary embodiments, the inhibitor of the Wnt-β-catenin signaling pathway is IWR1.

According to certain exemplary embodiments, the at least one additional growth factor is a protein of the TGF-β superfamily. According to certain exemplary embodiments, the TGF-β is selected from the group consisting of TGF-β-1, TGF-β-3, Activin-A and any combination thereof.

According to further aspect, the present invention provides a kit for expanding non-human-animal-derived PSCs aggregates comprising serum-free growth medium devoid of inactivated feeder layer cells; the growth factor bFGF; the growth factor TGF-β-3; Activin A; the small molecule IWR1; and instructions for growing conditions for expanding non-human-animal-derived PSCs aggregates.

According yet additional aspect, the present invention provides a method of reprogramming non-human-animal derived cells into iPSCs, the method comprising introducing into at least one non-human-animal-derived cell a combination of: (a) at least one reprogramming mRNA encoding a reprogramming factor; and (b) at least one double-stranded microRNA; thereby producing at least one iPSC.

According to certain embodiments, the method further comprises introducing into the at least one non-human-animal-derived cell at least one immune evasion mRNA.

According to certain embodiments, the at least one reprogramming mRNA is a synthetically modified mRNA.

According yet further aspect, the present invention provides a method of reprogramming non-human-animal derived cells into iPSCs, the method comprising introducing into at least one non-human-animal-derived cell a combination of: (a) at least one reprogramming mRNA; and (b) at least one inhibitor of at least one microRNA endogenous to the non-human-animal derived cell; thereby producing at least one iPSC.

According to certain embodiments, the method further comprises introducing into the at least one non-human-animal-derived cell at least one immune evasion mRNA.

According to certain embodiments, the at least one reprogramming mRNA encoding a reprograming factor and/or the at least one double-stranded microRNA are of human or non-human-animal origin.

According to certain embodiments, the non-human-animal is a bovine. According to these embodiments, the at least one reprogramming mRNA encoding a reprograming factor and/or the at least one double-stranded microRNA are of human or bovine origin. Each possibility represents a separate embodiment of the present invention.

Introducing the oligo- or polynucleotides of the invention into PSCs can be performed by any method as is known in the art.

According to the teachings of the present invention, the at least one mRNA is not integrated into the genome of the cell, thereby the produced iPSCs are not genetically modified.

According to certain embodiments, introducing the at least one reprogramming mRNA, and/or the at least one immune evasion mRNA and/or the at least one double-stranded microRNA and/or the at least one microRNA inhibitor is performed in a serum-free, animal-derived component-free liquid expansion medium. According to some embodiments, the medium is further animal-derived component free.

According to some embodiments, the method further comprises culturing the produced at least one iPSC in the serum-free liquid expansion medium to form a plurality of iPSCs. The serum-free liquid expansion medium is as described hereinabove. According to some embodiments, the serum-free liquid expansion medium used is supplemented with Rock inhibitor.

The reprogramming mRNA, the immune evasion mRNA, the double-stranded microRNA and the at least one microRNA inhibitor are as described hereinabove.

According to certain embodiments, the at least one non-human-animal-derived cell and/or the formed at least one iPSC is incubated at a temperature of between 37.5-39.5° C.

According to certain embodiments, the non-human-animal is of a species selected from the group consisting of ungulate, poultry, aquatic animals, invertebrate and reptiles. Each possibility represents a separate embodiment of the present invention.

According to certain embodiments, the ungulate is selected from the group consisting of a bovine, an ovine, an equine, a pig, a giraffe, a camel, a deer, a hippopotamus, or a rhinoceros.

According to certain exemplary embodiments, the ungulate is a bovine. According to these embodiments, the at least one bovine-derived cell and/or the formed at least one iPSC is incubated at 38.6° C., the average bovine body temperature.

According to some embodiments, the bovine-derived cells are obtained from bovine umbilical cord, bovine nasopharyngeal mucosa, and bovine blood. According to certain exemplary embodiments, the somatic bovine cells are collected by non-invasive techniques.

According to certain exemplary embodiments, the bovine-derived cells are obtained from bovine umbilical cord, wherein the cells are selected from the group consisting of endothelial cells, cord lining cells, Wharton's Jelly cells or a combination thereof. According to yet additional embodiments, the bovine-derived cells are obtained from beef cattle breed Belgium Blue. This breed is characterized by a double muscle phenotype due to a natural mutation in the myostatin gene.

The present invention also employs principles known from the art of PSCs aggregate formation; however, the present invention varies from the known art in several critical areas. First, the present invention provides a method to form aggregates of non-human animal derived PSCs, particularly bovine-derived PSCs. Second, the present invention provides a method of large-scale production of aggregates. Third, the present invention provides a method to form aggregates of non-genetically modified non-human-animal-derived PSCs, particularly bovine-derived PSCs.

The following examples are presented in order to more fully illustrate some embodiments of the invention. They should, in no way be construed, however, as limiting the broad scope of the invention. One skilled in the art can readily devise many variations and modifications of the principles disclosed herein without departing from the scope of the invention.

EXAMPLES

Example 1: Derivation of Pluripotent Bovine Embryonic Stem Cells (bESCs) from Flushed Embryos Cell Derivation Non-surgical procedure of flushing pre-implanted embryos after insemination is a routine procedure performed in conventional bovine breeding (Castro Neto A. S. et al, Theriogenology 63, 2005, 1249-1255). Such pre-implanted embryos were used to derive the embryonic stem cells (bESCs). Embryo flush was coordinated and conducted by Sion, Israeli company for artificial insemination & breeding Ltd. Flushed embryos were examined and counted under light microscope on site, then quickly transported to Applicant laboratory. To derive bESCs, pre-implanted embryos must be at the blastocyst stage. However, flushed embryos are at various embryonic developmental stage, (from early morula to expanded blastocyst) and at different grades (from poor to excellent). To reach blastocyst or enhanced blastocyst stage the flushed embryos were transferred to embryo maturation medium under microscope in a biological hood using micropipette, and incubated for 2-3 h. Embryos' stage and grade were evaluated (Stringfellow D. A., Givens M. D., Manual of the International Embryo Transfer Society, $4^{th}$ edition, Champaign (Ill.): International Embryo Transfer Society; 2010) and embryos at the blastocyst stage were selected. The Inner Cell Mass (ICM) of the embryos was then isolated using microsurgery (FIG. 1A). Isolated ICMs were then incubated at 38.6° C., 5% $CO_2$, monitored and documented for the establishment of bESCs colonies (FIG. 1B).

bESCs Characterization

Two exemplary lines of bESCs derived as described hereinabove, designated herein Alp 0501 and Alp 0505 were examined for pluripotency characteristics.

These bESC lines were grown in serum-free medium essentially as described in Bogliotti et al. (Bogliotti Y S et al., 2018. PNAS 115(9): 2090-2095). Briefly, cells were grown in the serum free medium mTeSR1® (STEMCELL Technologies Inc. Canada) supplemented with 2.5 μM IWR1, on inactivated mouse embryonic fibroblasts (iMEFs) as a feeder layer. Cells were passaged every 3-4 days with addition of Rho-associated kinase inhibitor (Rock inhibitor). The bESC morphology matches stem cell morphology and the cells grew in defined colonies.

bESC population doubling time (PDT) was measured by seeding the cells in 12-well plate (in triplicates) and counting their number on days 2, 3, and 4 following seeding (FIG. 2). Cell expansion reached 12-14-fold in one passage (4 days). Population doubling time (PDT) was calculated to be 26 hours for Alp 0501 and 24 hours for Alp 0505, which matches stem cell division rate.

The bESC lines were further examined for the expression of the pluripotency markers OCT4, SSEA4, Nanog, Sall4 and Dnmt3b.

Oct4 immunostaining was performed as follows:
1. Cells were washed with PBS and fixated by incubating with 4% Paraformaldehyde (PFA) for 20 minutes at room temperature.
2. Cell were permeabilized by incubating with 0.3% Triton-X for 10 minutes at room temperature.
3. Cells were washed with PBS.
4. Cells were blocked by incubating with 5% BSA and 0.1% Triton-X for 30 minutes at room temperature.

5. Cells were stained with Anti-Oct4 antibody (of Abcam) diluted 1:100 in 1% BSA and 0.1% Triton-X overnight at 4° C.
6. Cells were washed three times with PBS and analyzed by a fluorescent microscope.

Flow cytometry analysis for SSEA4 was performed as follows:
1. Cells were washed twice with PBS
2. Cells were incubated with 1:50 anti SSEA4 antibody (of R&D Systems) in staining buffer (of R&D Systems) for 1 hour at 4° C., protected from light.
3. Cells were washed twice with PBS and analyzed using flow cytometer.

Quantitative PCR (qPCR) analysis was performed as follows:
1. Total RNA was extracted from the cells using GeneJET RNA purification kit (Thermo Fisher Scientific).
2. Reverse transcription was carried out with RevertAid First Strand cDNA
Synthesis Kit (Thermo Fisher Scientific).
3. Quantitative PCR (qPCR) was performed to analyze expression of specific genes using specific primers designed for use in probe-based detection method.
4. All expression data were normalized to beta-actin. Relative quantification of fold change was calculated using the comparative Ct ($\Delta\Delta$Ct) method.

Figure 3B:
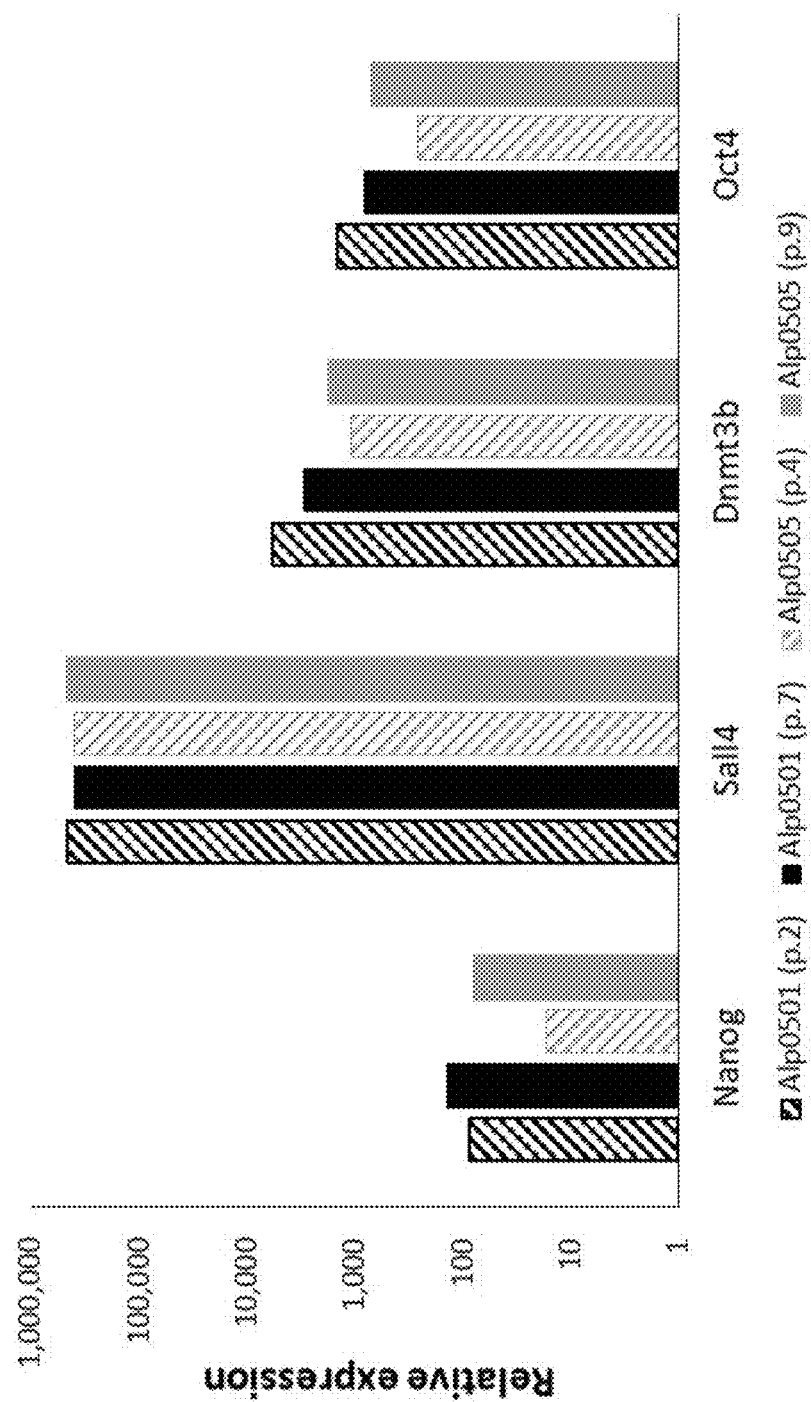

Oct4 immunostaining of the cells showed that the cells within the bES colonies are positively stained (data not shown). Flow cytometry was used to show that 80% of the cells in the culture are positive to the hallmark pluripotency marker SSEA4 (the majority of the unstained cells are the iMEF that usually constitute 15% of the cells in confluent culture) (FIG. 3A). High expression of the pluripotent markers Nanog, Sall4, Dnmt3b and Oct4 was shown by quantitative PCR (qPCR) analysis in the 2 cell lines in 2 passages for each (FIG. 3B).

Overall, based on cells morphology, growth rate, and pluripotency markers expression, the bESC lines Alp 0501 and Alp 0505 have been shown to be pluripotent.

Figure 4A:
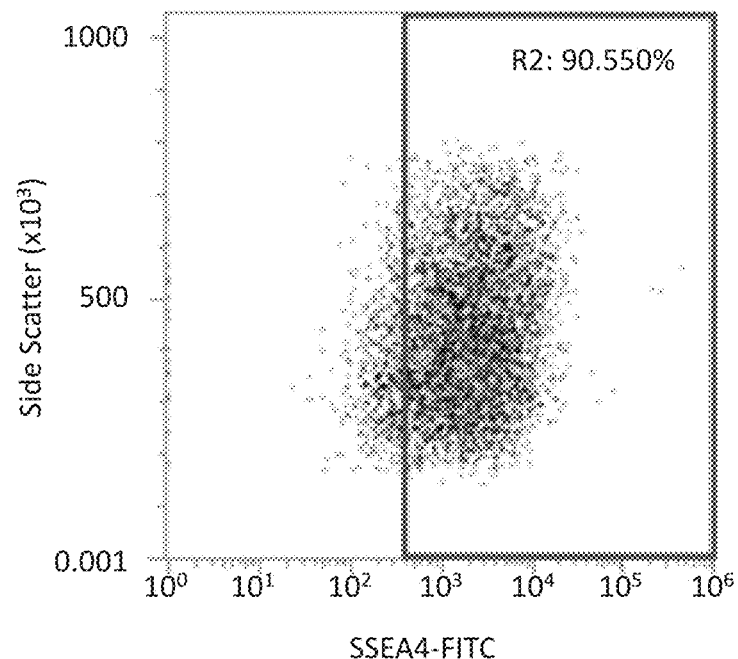
FIGS. 4A-4B shows expression percentage of the pluripotency marker SSEA4 by bESC grown in feeder-free culture measured by flow cytometry.
Figure 4B:
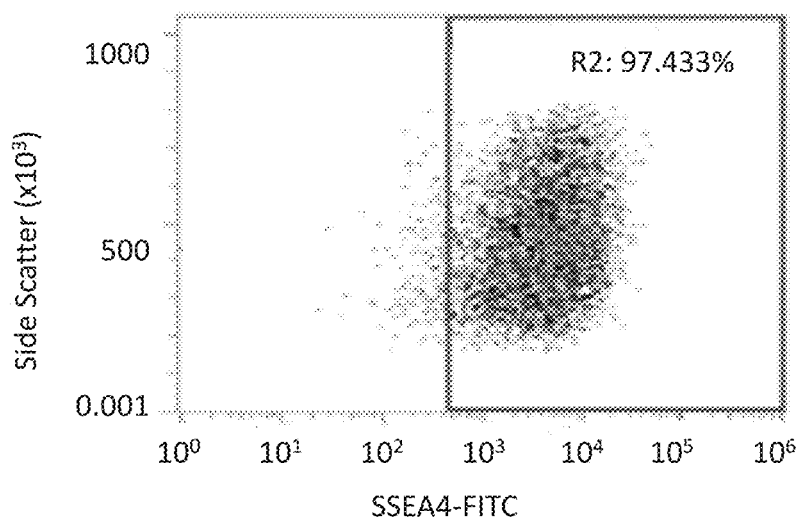

Example 2: Development of Feeder-Free Conditions for bESC Growth and Aggregation Feeder Free Growth Conditions The iMEF feeder layer supports growth and pluripotency of bESC by secreting necessary factors to the culture medium and supplying growth matrix to the cells. However, it is of significant importance to grow the bovine cells without additional cells, for simplicity, safety concerns and consumer acceptance when the cells are to be used in cultured food products. Coating the cell culture vessel with the coating matrix Vitronectin with the addition of Activin A to the culture medium successfully replaced the use of iMEF feeder layer. bESC derived from flushed embryos and grown as described hereinabove but with Vitronectin and Activin A instead of iMEF feeder layer were found to be positive to OCT4 using immunostaining (data not shown) and to SSEA4 using flow cytometry (FIG. 4).

Example 3: bESC Differentiation to Mesoderm

The intended use of the PSCs aggregates produced according to the teachings of the present is in the industry of cultured meat products. Cultured meat preferably comprises the various cells comprising the muscle tissue, including myoblasts, adipocytes, stromal and endothelial cells, all being derivatives of the mesoderm lineage. Accordingly, the ability of the PSCs to differentiate to mesoderm was examined.

Initial differentiation of bESC to mesoderm:
1. Cells were harvested and seeded for aggregates formation in 6-well plates as detailed in example 4 below.
2. The initial conditions were:
   a. bESC in the growth medium mTeSR1 (StemCell technologies)
   b. bESC in the growth medium Essential 8 (Thermo Fisher Scientific)
3. Four days after seeding, the medium was replaced to form the following conditions:
   a. Medium of bESC aggregates formed in mTeSR1 remained.
   b. Medium of bESC aggregates formed in Essential 8 medium was replaced to Essential 6 medium (Thermo Fisher Scientific)
Or—
   c. Medium of bESC aggregates formed in Essential 8 medium was replaced to Essential 6 supplemented with 8 µM CHIR 99021.
4. Cells aggregates were expanded for three days, after which they were collected and disaggregated using recombinant trypsin.
5. Cells pellet was used to extract RNA and perform qPCR as detailed in example 1, for Oct4 and Brachyury genes expression.

Figure 5:
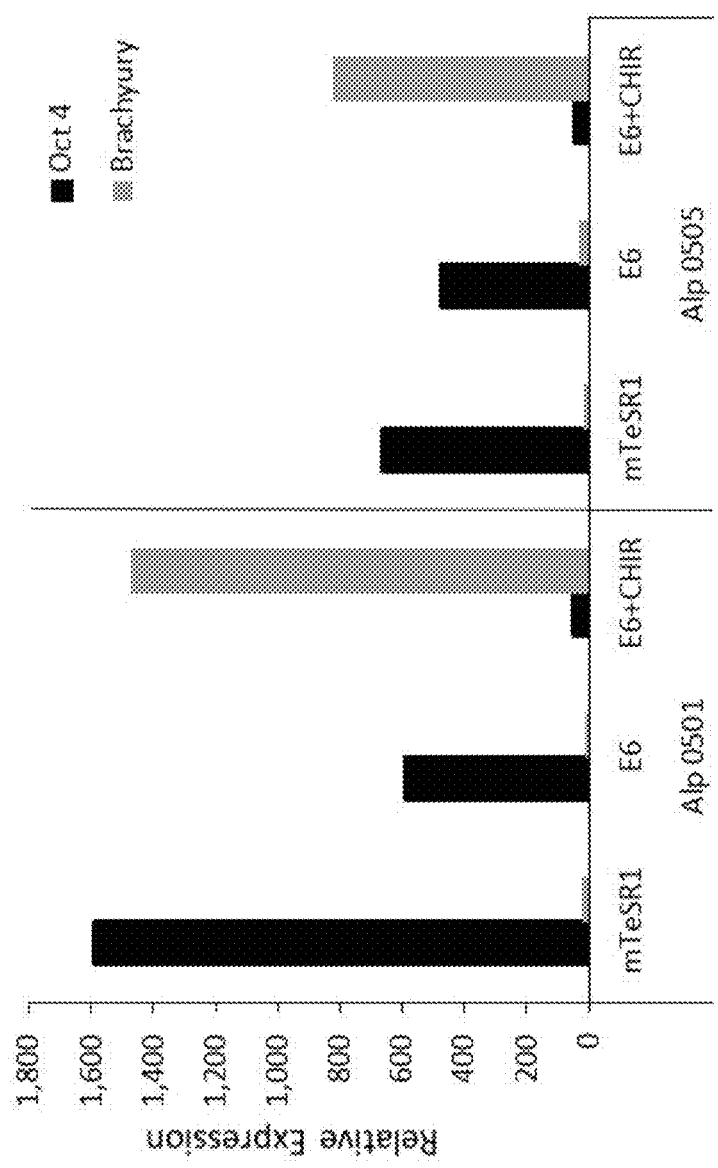
FIG. 5 demonstrated the differentiation capabilities of the bESC lines Alp 0501 and Alp 0505 determined by the expression of the pluripotency marker (Oct4) vs. the expression of the mesoderm marker (Brachyury).

As is shown in FIG. 5, replacing the mTeSR1 growth medium of the PSCs with E6 essential medium resulted in decreased expression of the pluripotency marker Oct4, for both bESC lines examined (Alp 0501 and Alp 0505). Addition of 8 µM CHIR 99021 led to additional decrease in Oct4 expression and to an increase in the initial mesoderm marker Brachyury, indicating that the cells have the ability to differentiate to mesoderm.

Example 4: Production of Aggregates of Non-Genetically Modified Bovine-Derived Pluripotent Stem Cells (PSCs)

1. Seeding Bovine-Derived PSCs in the Expansion Medium to Form Seeding Suspension Culture and PSC Aggregates bESCs were obtained as described in Example 1 above are used for preparing the 3D bESCs aggregate suspension culture of the invention in an expansion medium, a serum-free, liquid medium comprising a combination of growth factors.

1.1 Harvesting and Seeding of Cells:

iPSCs clones were grown on iMEF feeder layer in serum-free expansion medium supplemented with 50 ng/ml bFGF and 2.5 µM IWR1. Following 3-4 days in culture, when colonies confluence reached 70-80%, cells were detached using recombinant Trypsin to form single cells according to the following steps:
   a. Aspirating the medium from the initial monolayer culture in the biological hood.
   b. Rinsing the cells with PBS (—Ca/—Mg).
   c. Adding pre-warmed recombinant Trypsin solution.
   d. Incubating 3-5 minutes in the incubator at 38.6° C.
   e. Transferring the vessel into the biological hood and adding Soybean anti-trypsin at a 1:50 (v/v) ratio. Tapping the sides of the vessel with the palm of a hand to assist detachment. Adding basal media (for wash-without supplements) and gentle pipetting, 3-4 times, to dissociate the cells to singles.

f. Collecting the cells from the vessel and transferring them to an appropriate tube. Centrifugation of the cells, removal of the supernatant from the cell pellet and resuspension in fresh medium.

g. Counting the cells and seeding in 3D suspension at a concentration of $0.2\text{-}0.5 \times 10^6$ cells/ml in an appropriate culture vessel (see section 1.2 and 1.3 below). Adding 10 μM inhibitor of Rho-associated protein kinase (Rock Inhibitor, Y27632) and 1× Poloxamer 188 solution (Pluronic F-68).

h. For reseeding to 2D conditions seed at 20-50K cells/cm² density on iMEF.

Figure 6A:
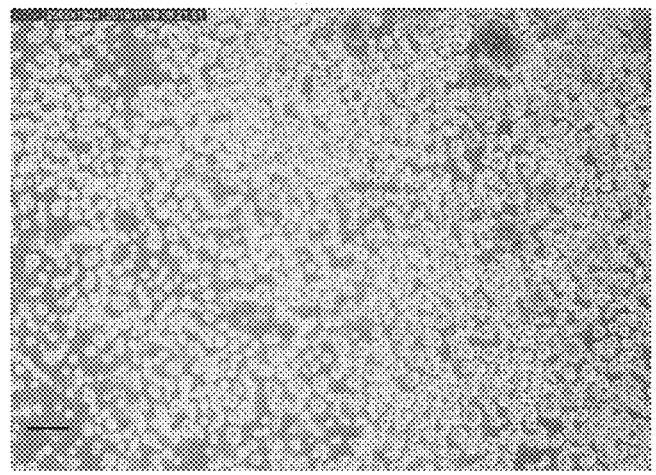
FIGS. 6A-6C demonstrate bESC aggregate formation and expansion in 6-well plate.
Figure 6B:
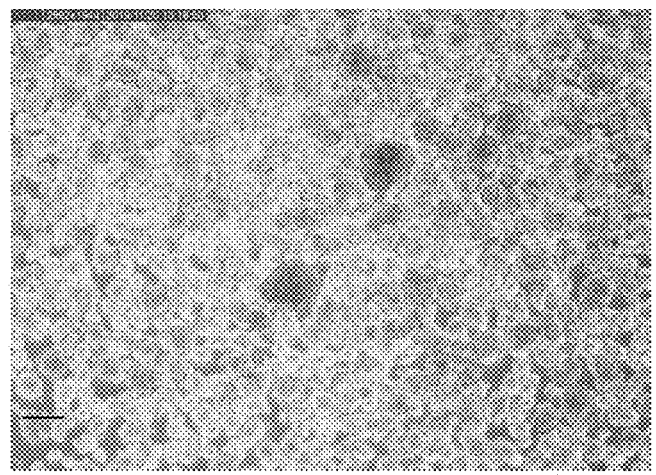
Figure 6C:
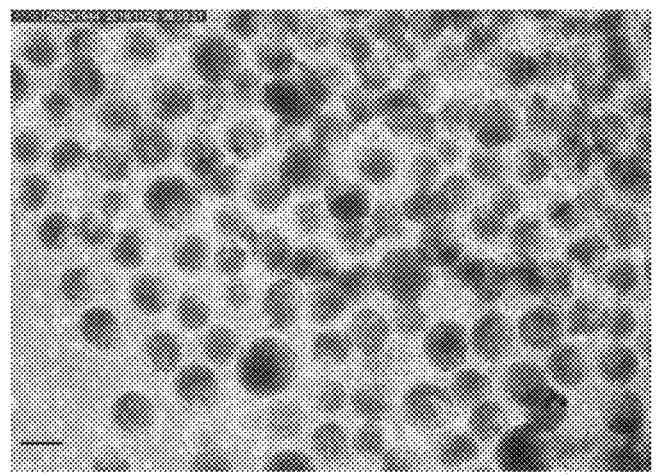

1.2 Aggregates Formation in 6-Well Plate:

bESCs were seeded at $0.3 \times 10^6$ cells/ml in 3 ml expansion medium per well, supplemented with 50 ng/ml bFGF, 2.5 μM IWR1, 10 μM inhibitor of Rho-associated protein kinase and in ultra-low attachment 6-well plate. Cells were incubated for 2-7 days at 38.6° C., 5% $CO_2$ and 80% humidity, at a shaking speed of 90-95 rpm. The medium was changed daily from the second day of seeding by carefully aspirating 80% of the used medium and replacing with fresh expansion medium, fresh medium doesn't contain 10 μM inhibitor of Rho-associated protein kinase. Aggregates were monitored on days 1, 2 and 7 following seeding (FIG. 6). Aggregates diameter size one day following seeding was 38±22 μm (FIG. 6A). Following 2 days in culture, aggregates size increased to 58±36 μm (FIG. 6B). Day 7 wasn't measured due to technical problems but aggregates continued to grow to ~200 μm (FIG. 6C).

Example 5: bESC Aggregate Formation in a Stirred Tank Bioreactor System

Figure 7:
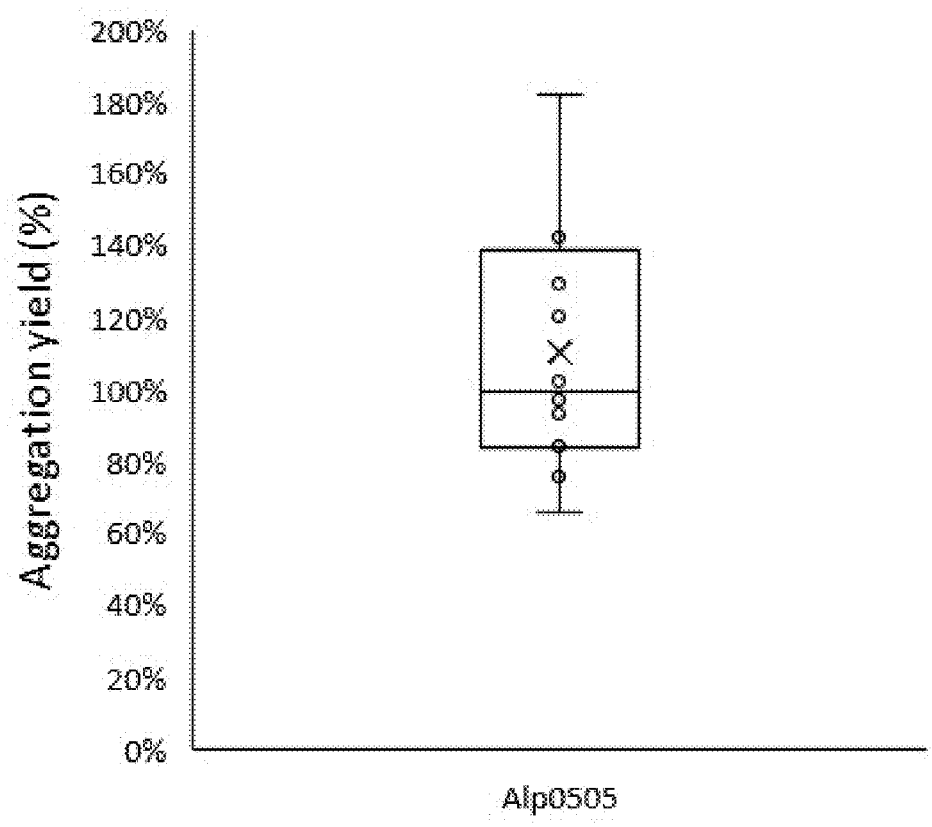
FIG. 7 shows aggregation yield of bESC in stirred tank (STR) bioreactor (% live/live cells).

After examining the aggregation feasibility of bESCs, growth in stirred tank bioreactor system was examined. The stirred tank bioreactor system allows monitoring and controlling additional factors (such as pH, dissolved Oxygen ($DO_2$) and connection to various pumps to feed/harvest media), which are important for a long-term and automated process. bESCs were inoculated at an initial concentration of 0.2-0.5 million cells/ml in 70-100 ml of expansion medium per well, supplemented with 50 ng/ml bFGF, 2.5 μM iWR1, 10 μM inhibitor of Rho-associated protein kinase. The pH was set to 7.0 and $DO_2$ was set to 40-70%. Impeller rotation speed was set to 90-190 rpm. Runs were performed with clone Alp0505. As is demonstrated in FIG. 7, average of 104% in 12 separate runs was observed. Aggregation yield is calculated as the percentage of live cell concentration post 24 h from inoculation relative to live cell concentration at seeding (live/live %). Having >100% yield in multiple runs means that not only did most of the bESCs aggregate, but they also began to proliferate and expand in the aggregate within the first 24 h.

Figure 8A:
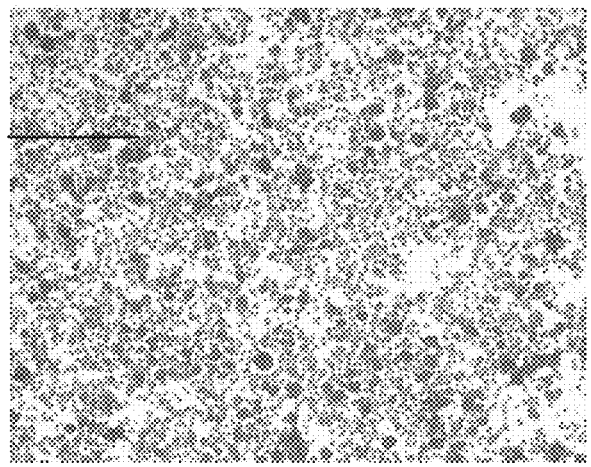
FIGS. 8A-8C show bESC aggregate expansion in stirred tank (STR) bioreactor after 1, 3 and 4 days of growth (FIG. 8A-C, respectively). Representative images, scale bar=650 µm.
Figure 8B:
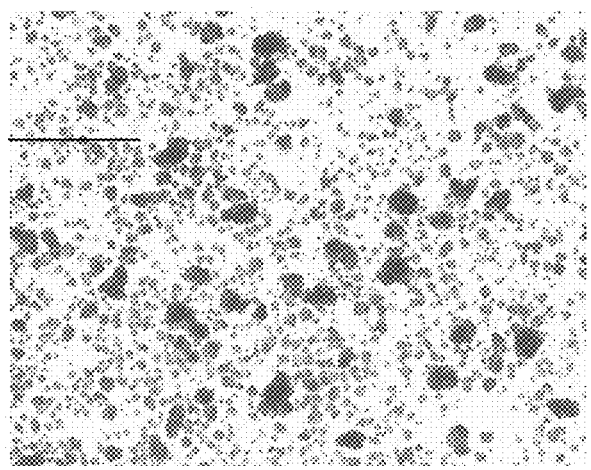
Figure 8C:
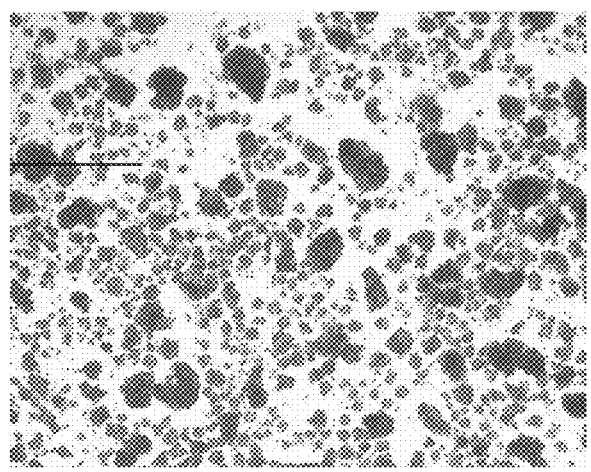
Figure 8D:
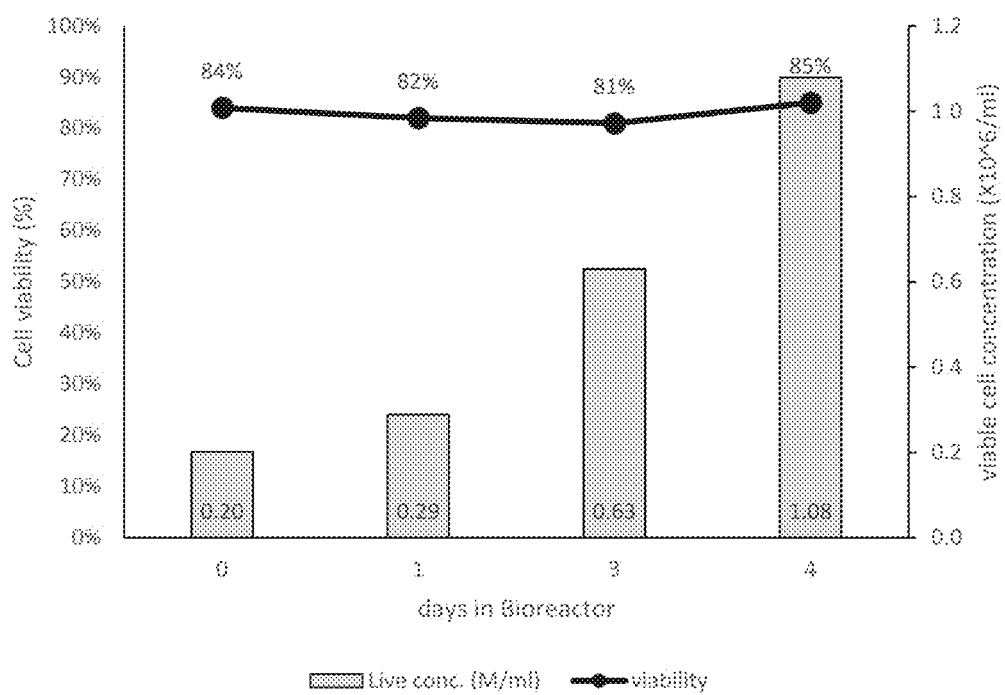
FIGS. 8D-8E show cell concentration and viability (FIG. 8D) and average aggregate diameter (FIG. 8E). Pluripotency (presented as SSEA4% expression) overtime is indicated in FIG. 8E.
Figure 8E:
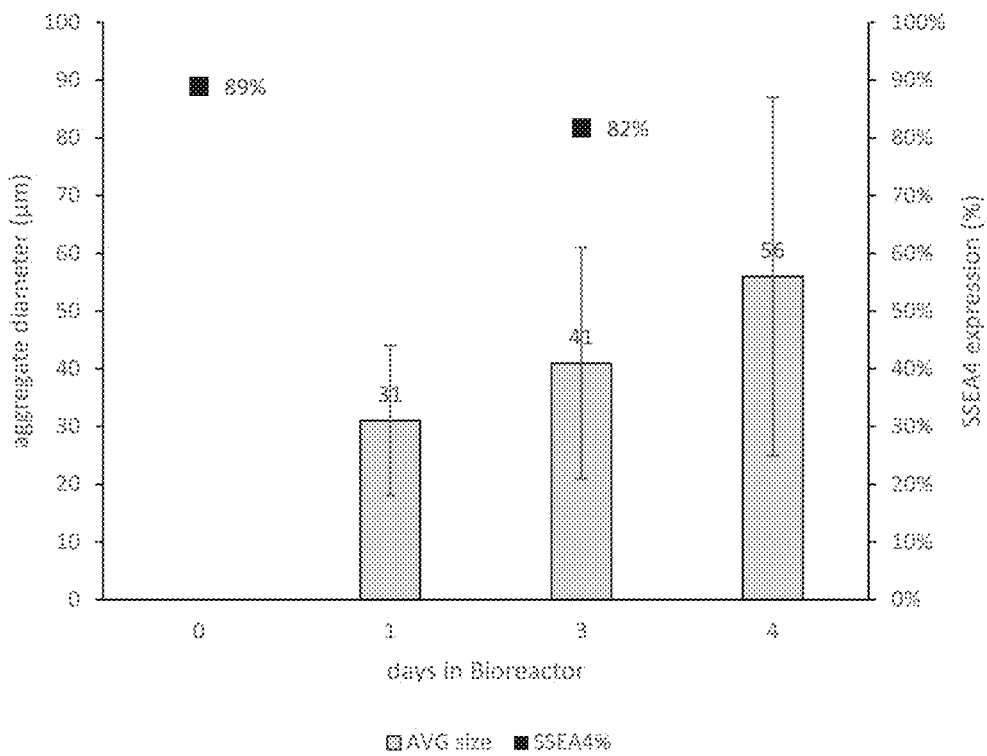

Example 6: Expansion of bESCs Within the Aggregates in a Stirred Tank Bioreactor System After aggregation yield of >70% was successfully reached cell expansion in aggregates was examined. To facilitate cell proliferation, the medium was freshly supplemented with 25 ng/ml bFGF (to the entire working volume), taking in account that from the previous day all bFGF was used or was heat-inactivated. Also, the cell metabolism was follow up and glucose was added if the concentration measured was <1 gr/L. These steps were performed manually in a fed-batch manner; yet after the aggregates passed diameter of 45 μm the medium was automatically exchanged via a perfusion filter-system (typically after 2-3 days of growth). A 5.4-fold expansion in the bioreactor was observed, from seeding $0.2 \times 10^6$ viable cells/ml to $1.08 \times 10^6$ viable cells/ml on day 4 (in 100 ml) as is demonstrated by an increase in cell concentration (FIG. 8D). In parallel the aggregates increased in diameter from 31 μm on day 1 to 56 μm on day 4 (FIGS. 8 A-C, 8E). Pluripotency was analyzed on day 0, 3 and 5 and remained >70% in all time points (FIG. 8D, data for day 5 not shown, % SSEA4=83%). Theoretical calculations based on aggregate initial size, cell number and the fold expansion observed after 4 days 100-fold expansion of cells to $2.5 \times 10^7$ cells/ml and more is expected as is demonstrated in Table 1 hereinbelow.

TABLE 1

| | Theoretical calculation of aggregate expansion | | | | | | | |
|---|---|---|---|---|---|---|---|---|
| Group | Cell/Agg. Diameter (μm) | Cell/Agg. Radius (μm) | Volume (μm³) | Porosity Factor | Final Volume (μm³) | No. of Cells/Agg. | Exp. Factor | Cell Conc. (×10⁶) |
| Single Cell | 18 | 9 | 3052 | 0 | 3052 | 1 | NA | 0.2 |
| Agg. After 1 Day | 36 | 18 | 24417 | 0.8 | 19533 | 6 | NA | NA |
| 5M/ml Agg. | 106 | 53 | 623298 | 0.8 | 498639 | 163 | 26 | 5.1 |
| 25M/ml Agg. | 180 | 90 | 3052080 | 0.8 | 2441664 | 800 | 125 | 25 |
| Final Agg. | 260 | 130 | 9198107 | 0.8 | 7358485 | 2411 | 377 | 75.3 |

Agg.—Aggregate;
Conc.—Concentration

Example 7: Re-Aggregation of Small Aggregates and Single Cells

According to some embodiments of the present invention, some of the PSC aggregates serve as a continuous reservoir for cell expansion-cycles in large-scale liquid culture conditions via disaggregation and re-aggregation procedures. It is further of significant importance for the production of PSC aggregates at a large-scale, particularly of bovine derived PSC aggregates for use in the production of cell grown meat products, that the entire procedure of forming aggregates, including the steps of repeated dis-aggregation and re-aggregation, is performed in a closed system. Closed system refers to either performing the steps of disaggregation and re-aggregation in the same vessel without discarding the aggregate dissociation solution or using, for example, cell retention/separation devices in a closed system, connected to the vessel and forming a loop allowing to remove said dissociation solution and keep a sterile environment and automated process. cell retention/separation devices are generic and can be added-on to any vessel system ranging from 3 to 2000L.

Figure 9A:
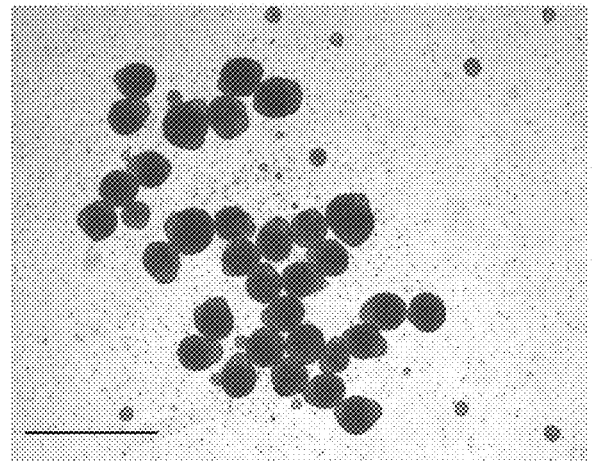
FIGS. 9A-9B demonstrates the process of disaggregation and re-aggregation.
Figure 9B:
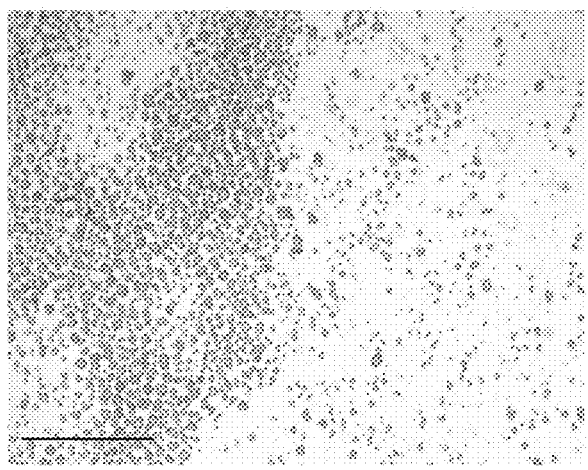

In initial re-aggregation trials, small aggregates/single cells obtained from disaggregation of 4 and 7 days old aggregates re-seeded in a fresh medium formed only few, very large aggregates. Also, the pluripotency of the cells after such re-aggregation was not maintained. In further re-aggregation trials, small aggregates/single cells obtained from disaggregation of 3 days-old aggregates (FIG. 9A) were re-seeded in a medium containing dissociation reagents (proteolytic enzymes, DNA degrading enzyme and a chelating agent). Unexpectedly, the presence of the dissociation reagents enables re-aggregation, and the formed large number of small aggregates (FIG. 9B) enabling proliferation of the cells and expansion of the aggregates.

Example 8: Isolation of Stromal Mesenchymal Cells from Bovine Umbilical Cord

1. Bovine umbilical cord (bUC) and placenta were collected from the collection site wrapped in a cloth soaked with saline and transferred to the lab at 4° C. The processing of the tissue began in less than of 2-4 hours from collection.

2. The tissue was placed in a 150-mm petri dish kept on ice in a biosafety cabinet and rinsed multiple times with ice-cold PBS with antibiotics (comprising of: Pen-strep solution (Pen-100 u/ml, Strep-0.1 mg/ml), Gentamycin solution (5 mg/ml), Amphotericin B (0.25 mg/ml)), using a needle and syringe, to remove blood clots.

Figure 10A:
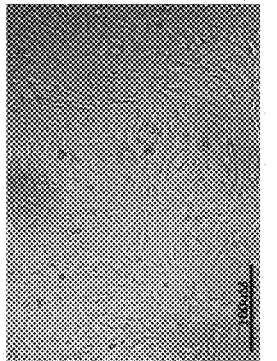
FIGS. 10A-10D shows representative pictures of various stages in the isolation of umbilical cord cells.

3. The bUC (FIG. 10A) was separated and cut longitudinally, completely exposing the blood vessels and surrounding Wharton's Jelly (WJ), without disturbing the epithelium.

Figure 10B:
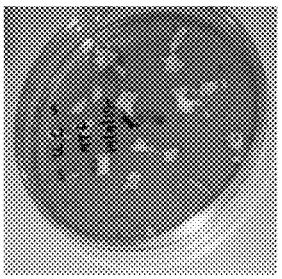

4. The WJ (FIG. 10B) was scraped away from the blood vessels and inner epithelium and transferred into a petri dish. The blood vessels were removed.

Figure 10C:
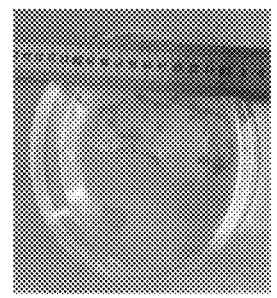

5. The tissues were cut (FIG. 10C) (WJ and cord lining (CL)) into 1- to 2-mm pieces with mechanical shearing and enzymatic dissociation.

6. The WJ tissue pieces were washed 4 times with PBS with antibiotics (as above). 30-40 tissue pieces were plated on a 150-cm tissue culture dish and added with complete medium (comprising of: DMEM (with glutamine and glucose), Pen-strep solution 1%, Gentamycin solution 1%, Fetal Bovine Serum 10%) or serum-free medium with or without cell adhesion matrix, to a total volume of 20 ml. The culture was then incubated at 38.6° C. for 2-3 days to allow for the adherence of tissue pieces.

7. The CL tissue pieces were washed 4 times with PBS with antibiotics (as above). The tissue pieces were spread all-over the plate. The culture was then incubated at 38.6° C. for 2-3 days to allow for the adherence of tissue pieces.

8. The complete medium was changed after 2-3 days of incubation, for all treatments.

Figure 10D:
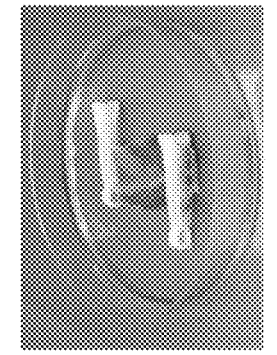

9. The cells from the explants were explored for the appearance of outgrowth on a daily basis; cell growth was evident from the adherent explants after 7-10 days of incubation for the bovine-derived CL. From this point onwards, the medium was replaced every 3 days or as needed and the cells were expanded using trypsin at 80% confluency (FIG. 10D).

10. After 1-3 passages the cells were pooled and resuspended in growth media with 10% DMSO and frozen as cell banks in the concentration of $0.2$-$1.5*10^6$ cells per cryogenic tube (cryovial).

11. The cells were thawed for 1-2 minutes at 38.6° C. and counted for their viability. The viability at thaw was above 73%.

The resulted umbilical cord lining cells from both cell banks used have typical characteristics of mesenchymal stromal cells with a fibroblasts-like morphology and high proliferation rate at lower passages till P8/P9 and they become senescence with larger cytoplasm at P10. PCR analysis of the cord lining cells showed that the cells are positive to the typical markers of the mesenchymal cells among them NCAD, THY1/CD90 and NCAM/CD146.

Example 9: Isolation of Bovine Embryonic Fibroblasts (BEF) and Myoblasts (BEM)

1. Bovine embryo's hindlimb was harvested from fetus and transferred to the lab in a 50 ml tube with cold PBS (—Ca/—Mg)+1% Pen-Strep.

2. In the biological hood, the blood vessels, fat tissue and connective tissues were removed from the muscle tissue using stainless-steel scissors and tweezers.

3. The selected muscle tissue pieces were transferred to 150 mm dish with fresh PBS and the solution was exchanged twice.

4. All fluids were removed and selected amount of tissue was cut into paste-like consistency.

5. The paste was transferred into a 50 ml tube (=tube #1) containing 30 mg Collagenase (type1, Gibco) in 10 ml DPBS (—Ca/—Mg), and filtered through a 0.2 µm filter.

6. The 50 ml tube was sealed with parafilm and placed horizontally on orbital shaker (90 RPM) at 38.6° C. for 1 hr.

7. Trypsin was heated for 15 min. prior the end of step 5.

8. Tube #1 was centrifuged at 130 RCF for 1.5 minutes, then the upper sup (containing cells+fat) was transferred into a new 50 ml tube (=tube #2).

9. 20 ml of pre-warmed Trypsin were added to tube #1 (containing residual tissue) and placed horizontally on orbital shaker (90 RPM) at 38.6° C. for 20 minutes.

10. In parallel, tube #2 was centrifuged for 5 minutes at 285 RCF (pelleting cells+tissue residues), then the sup was discarded and the pellet was re-suspend with 10 ml standard media.

11. Once the trypsinization is finished (step #8), tube #1 was centrifuged for 5 minutes at 285 RCF.

12. Most of the sup from tube #1 (up to the 5 ml mark) was removed.

13. Standard media was added up to the 10 ml mark to tube #1.

14. The tissue pieces were mechanically broken by pipetting the entire volume in tube #1 ~X15 times with a 13 ml pipette.

15. Tube #1 was centrifuged for 1.5 minutes at 130 RCF

16. The middle phase of tube #1 (~5 ml) was collected and transferred into tube #2.

17. Steps #14 to 17 were repeated twice more (a total of 3 times)

18. Finally, the cell pool tube #2 was centrifuged at 285 RCF for 5 minutes to pellet all collected cells.

19. The sup was discarded and cells were resuspended in 20 ml standard media.

20. The cell suspension was passed through a 40 μm strainer into 2×100 mm dishes (~10 ml each).

21. Both dishes were stationary placed in the incubator at 38.6° C. 5% $CO_2$ for 2 hours.

22. 1-hour prior finishing, 2×100 mm dishes were pre-coated with 0.1% gelatin at room temperature.

23. Post 2 hours from plating the cells dishes were transferred back to the hood and the upper sup was carefully discarded as much as possible (contains dead unattached floating cells).

24. The dishes were slightly tilted to keep the tilt angle fixed. The dish was then slowly rinsed with pre-warmed 20% FBS media and transferred to a 15 ml tube (myoblast pool). Rinsing was repeated at least twice more (a total of 3 times).

25. Finally, all the cells were seeded into the freshly coated 100 mm dishes.

26. The cells that were left attached to the non-coated TC plate are the desired fibroblasts.

Example 10: Cell Differentiation to Adipocytes

The conditions in which bovine cells differentiate to adipocytes required serum free medium supplemented with fatty acids and a combination of bFGF 20 ng/μl, IWR1 2.5 μM and Rock Inhibitor 10 μM (adipocyte differentiation medium).

Materials and Solutions
1. BEF culture at maximum passage 6
2. Standard medium (DMEM HG, 10% FBS, 4 mM L-Glutamine, 1% Pen-Strep)
3. PBS, (—)$Ca^{+2}$, (—)$Mg^{+2}$, BI 02-023-1A
4. Serum free growth media:
   ES medium (DMEM/F12 medium, 15% KOSR Gibco, 1% NEAA, 4 mM L-Glutamine, 0.1 mM—2-Mercaptoethanol, 1% Pen-Strep)
5. Adipocyte differentiation media:
   5.1 Serum free growth media
   5.2 bFGF 20 ng/μl
   5.3 IWR1 2.5 μM
   5.4 Rock Inhibitor 10 μM Procedure
Day 0:
1. Seed BEF culture at a concentration of 15,000 cells/$cm^2$ in Standard medium.
2. Incubate for overnight at 38.6° C., 5% $CO_2$.

Day 1:
Discard medium and add freshly made adipocyte differentiation medium.

Day 3-9:
Change adipocyte differentiation medium every other day for the next days.
Medium has to be prepared freshly every time.

Day 5-10:
Inspect the culture daily and expect to visualize the oil vesicles.

Day 11-30:
An increase in adipocytes differentiation yield is expected.

Fixing and Coloring the Adipocytes:
1. To make Oil Red O Working Solution: add 3 parts of Oil Red O Stock Solution to 2 parts of $dH_2O$
2. Mix well, and allow to sit for 10 minutes.
3. Filter with 0.2 μm syringe filter or Whatman No. 1 paper or equivalent.
4. Add Isopropanol (60%) to each well and incubate for 5 minutes.
5. Remove isopropanol and add Oil Red O Working Solution to completely and evenly cover the cells (1 ml/well in six well plate)
6. Rotate plate or dish and incubate for 10-20 minutes.
7. Remove Oil Red O solution and wash 2-5× with $dH_2O$ as needed until excess stain is no longer apparent.

Figure 11:
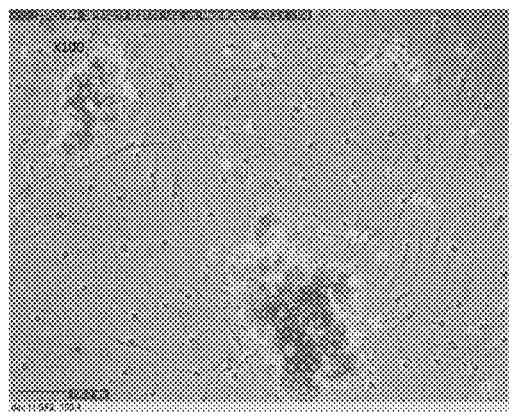
FIG. 11 shows a representative picture of adipocytes differentiated from cells within a culture of BEFs. The differentiated cells appear darker due to staining by Oil red O. Oil red O stains triglycerides and lipids.

When exposed to the adipocyte differentiation media described above, Bovine embryonic fibroblasts (BEF) culture showed differentiation to adipocytes. The differentiated cells were stained by Oil red O staining. Oil red O stains triglycerides and lipids (FIG. 11). The conditions in which the cells differentiate to adipocytes requires serum free medium supplemented with fatty acids and a specific combination of bFGF 20 ng/μl, IWR1 2.5 μM and Rock Inhibitor 10 μM (adipocyte differentiation medium).

The appearance of adipocytes has started on day 5 of culturing the cells with the adipocyte differentiation medium. The adipocytes differentiation increased over time.

bFGF among other roles, induces the expression of PPARgamma2, a key transcription factor in adipogenesis. IWR-1 is a WNT signaling inhibitor. WNT signaling represses adipogenesis by blocking induction of Peroxisome proliferator-activated receptor gamma (PPARgamma) and CEBPA. The addition of IWR-1 inhibits the WNT pathway and accordingly adipogenesis is induced. The ROCK Inhibitor, Y-26732 Enhances the Survival and Proliferation of cells.

Bovine stromal stem cells isolated from fat tissue were also showed to efficiently differentiate to adipocytes using the adipocyte differentiation medium described above Example 11: Reprogramming of Bovine Cells Using Episomal Plasmid BEFs were reprogrammed to bovine induced pluripotent stem cells (biPSCs) using a single episomal plasmid (CoMiP Plasmid #63727) encoding the human sequences of the four canonical reprogramming factors (Oct4, Sox2, Klf4 and c-Myc) together with a dTomato red color marker, all controlled by one promoter. The use of plasmid DNA-based reprogramming method dramatically reduces the potential risk of random genomic integration of the transfected DNA into the host cell genome, and most human iPSC cells generated by plasmid transfection were found to be free from integration (Diecke S 2015, Sci. Rep., Article number: 8081).

BEF cells at passage 4 (P4) were transfected by electroporation with 12 μg of the CoMiP plasmid. To increase cell survival, CoMiP plasmid was purified using an endotoxin free Qiagen plasmid miniprep kit.

Figure 12A:
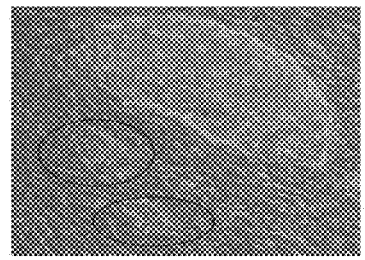
FIGS. 12A-12C demonstrates growth of biPSC clone on iMEF in 12-well plates.

Transfected cells were immediately seeded on 0.1% gelatin-covered 10 cm plates in DMEM 10% FBS medium, and the transfection efficiency was evaluated a day later by the red fluorescent protein expression of the dTomato color marker within the CoMiP plasmid. Cells were allowed to recover from electroporation for 4 days. Following recovery, cells were trypsinized and seeded on top of irradiated mouse embryonic feeder layer (iMEFs). The next day cell medium was changed to serum free expansion medium comprising 2.5 μM human IWR1 and 20 ng/ml human bFGF (also referred to as "reprogramming medium"). 10 μM rock inhibitor was added at seeding. Cell medium was refreshed every other day. Embryonic stem cell (ES)-like colonies appeared in cultures 2 weeks following transfection (FIG. 12A).

Figure 12B:
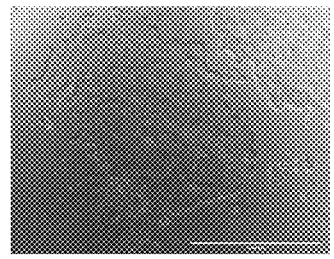
Figure 12C:
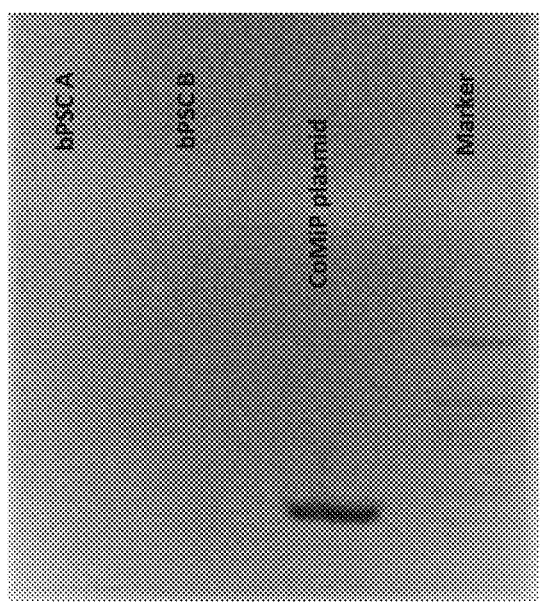

Single colonies were manually picked and expanded for cell-bank and characterization. The iPSCs maintained ES-like morphology following prolonged passaging. Following clone expansion iPSCs were adapted for feeder-free growth condition and presented growth on Vitronectin in expansion medium supplemented with 2.5 µM IWR1 and 50 ng/ml human bFGF (FIG. 12B).

iPSCs were screened for possible plasmid integration event by PCR analysis, using primers targeting the junction region between OCT4 and KLF4 within the reprogramming vector, and found to be free from integration (FIG. 12C).

Example 12: Reprogramming of Bovine Cells Using Modified mRNA

BEF cells were induced to reprogram using RNAs encoding the mRNA of the four canonical reprogramming factors Oct4, Sox2, Klf4 and c-Myc according to the bovine genome sequences together with two of the bovine microRNA cluster sequences encoding miR203b and miR302d.

To reduce cell toxicity to the RNA transfection, cells were additionally transfected with mRNA encoding the B18R vaccinia virus sequence. For transfection efficiency and mRNA expression evaluation, cells were transfected with modified mRNA encoding a mCherry red color marker.

The mRNA modifications ($\Psi$5mC on all bases, CleanCAP AG, 120-nt Poly-A) were used in order to get an enhanced translation and a higher stability of the mRNA molecules that we have designed.

RNA Transfection Protocol:

1. BEFs were harvested, seeded (10K cells/cm$^2$) in DMEM+10% FBS+1% Pen-Strep medium and incubated over night at 38.6° C.
2. The medium was changed to DMEM+10% FBS without pen-strep and cells were returned to the incubator.
3. A transfection mix was prepared (per 100K cells): mRNAs and micro RNAs were diluted in 250 µl Opti-MEM serum free medium. Transfection reagent was added and the reaction was mixed and incubated for 5 minutes at RT.
4. Transfection mix was added drop by drop directly into the cell medium.
5. Cell were incubated over night at 38.6° C.
6. The transfection was performed 4 times in four consecutive days (Steps 2-5×4)
7. Following the last transfection, medium was changes and cells were incubated at 38.6° C. for 2-3 days to allow recovery.
8. Cells were harvested and counted for their viability.
9. 10$^6$ cells were set aside for RNA isolation and qPCR analysis of OCT4 mRNA expression level.
10. Cells were seeded 5K-10K cells/cm$^2$, on-top of inactivated mouse embryonic feeder layer (iMEF), in DMEM+10% FBS+1% Pen-Strep medium. Cell pellet were taken as well.
11. Cells were incubated over night at 38.6° C.
12. Cell medium was aspirated and replaced with expansion medium, supplemented with: 2.5 µM human IWR, 20 ng/ml human bFGF and 10 µM rock inhibitor.
13. Cell medium was refreshed every other day for 3 weeks, cultures were screened for the appearance of ES-like colonies.

Figure 13A:
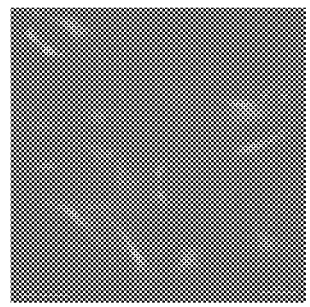
FIGS. 13A-13C shows BEF cells efficiently transfected with modified mRNAs, demonstrated by mCherry and bovine OCT4 expression. Fluorescence (FIG. 13A) and bright-field (FIG. 13B) images of BEF cells transfected with modified mRNAs encoding bovine OSKM, mCherry and B18R. Fluorescent images show the transfection efficiency 24 h following the first mRNA transfection.
Figure 13B:
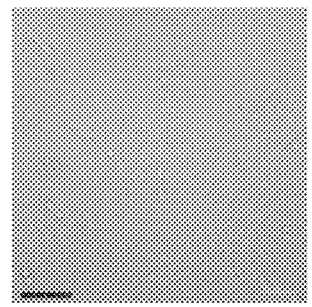
Figure 13C:
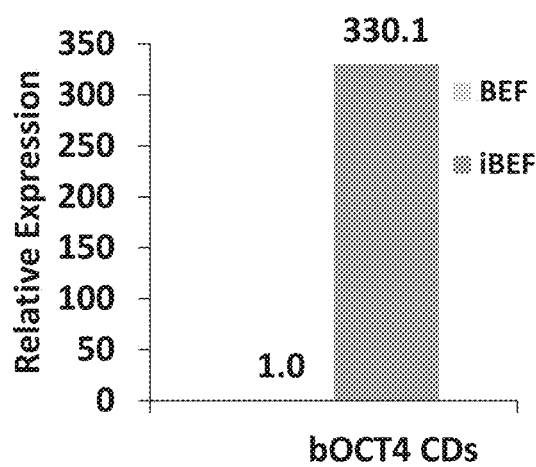

To evaluate the transfection efficiency, the cells were analyzed for both mCherry and OCT4 expression. mCherry expression was evaluated using a fluorescent microscope, 24 hrs. post each transfection (FIG. 13A fluorescent filter, 13B bright field). Following the fourth transfection cells were allowed to recover over the weekend, and then cells were harvested using trypsin and cell pellets were taken for qPCR analysis, which showed high transcript level of OCT4 in the BEFs that were induced by reprograming mRNA and miRNA (iBEF) (FIG. 13C).

The foregoing description of the specific embodiments will so fully reveal the general nature of the invention that others can, by applying current knowledge, readily modify and/or adapt for various applications such specific embodiments without undue experimentation and without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. The means, materials, and steps for carrying out various disclosed functions may take a variety of alternative forms without departing from the invention.

The invention claimed is:

1. A method of producing aggregates of non-genetically modified non-human-animal-derived pluripotent stem cells (PSCs) comprising the steps of:
   a. seeding at least one PSC in an expansion medium, the expansion medium is a serum-free liquid medium comprising a combination of the growth factor bFGF and at least one of (i) at least one additional growth factor and (ii) at least one small molecule selected from the group consisting of an inhibitor of the Wnt-β-catenin signaling pathway, CHIR 99021 (C22H18Cl2N8), PD 0325901 (C16H14F3IN2O4), and A 83-01 (C25H19N5S), to form a seeding suspension culture; and
   b. growing the suspension culture under conditions enabling aggregate formation and aggregate expansion, thereby forming homogenous aggregates of the PSCs.

2. The method of claim 1, wherein step (b) of growing the suspension culture comprises performing at least once the steps of (i) disaggregating the formed homogenous aggregates into smaller aggregates and/or single cells and (ii) re-aggregating the smaller aggregates and/or single cells to re-form homogenous aggregates.

3. The method of claim 1, wherein the method is performed in a closed system.

4. The method of claim 1, wherein the expansion medium comprises a combination comprising bFGF and at least one small molecule.

5. The method of claim 1, wherein the at least one additional growth factor is a protein of the transforming growth factor beta (TGF-β) superfamily.

6. The method of claim 1, wherein the expansion medium comprises a combination comprising bFGF and at least one additional growth factor, wherein the at least one additional growth factor is a protein of the TGF-β superfamily selected from the group consisting of TGF-β-1, TGFβ-3, and Activin-A.

7. The method of claim 1, wherein step (a) of seeding the at least one PSC further comprises encapsulating the at least one PSC within a particle and seeding a plurality of the particles within the expansion medium.

8. The method of claim 1, wherein the suspension culture is grown at a temperature which is the body temperature of the non-human-animal species from which the cells are derived.

9. The method of claim 1, wherein the PSC aggregates formed have an average diameter of from about 50 µm to about 500 µm.

10. The method of claim 1, wherein the non-human-animal is bovine, and wherein the bovine PSCs are embryonic stem cells produced by a method comprising the steps of:
  i. obtaining at least one bovine pre-embryo;
  ii. culturing the at least one pre-embryo to reach blastocyst or enhanced blastocyst stage;
  iii. obtaining at least one cell from the blastocyst; and
  iv. culturing the at least one cell in a culture medium comprising a combination of the growth factor bFGF, and at least one of (i) at least one additional growth factor and (ii) at least one small molecule selected from the group consisting of an inhibitor of the Wnt-β-catenin signaling pathway, CHIR 99021 (C22H18Cl2N8), PD 0325901 (C16H14F3IN2O4), and A 83-01 (C25H19N5S), to obtain a plurality of bovine-derived embryonic stem cells.

11. The method of claim 1, wherein the non-human-animal PSCs are induced pluripotent stem cells (iPSCs) produced by a method comprising introducing into at least one non-human-animal-derived cell a combination of:
  a. at least one reprogramming mRNA encoding reprogramming factor; and
  b. at least one double-stranded microRNA; or
  C. at least one inhibitor of at least one microRNA endogenous to the non-human-animal-derived cell;
thereby producing at least one iPSC.

12. The method of claim 11, wherein the method further comprises introducing into the at least one non-human-animal-derived cell at least one immune evasion mRNA.

13. The method of claim 11, wherein introducing the at least one reprogramming mRNA, and/or the at least one immune evasion mRNA and/or the at least one double-stranded microRNA and/or the at least one miRNA inhibitor is performed in a serum-free liquid expansion medium, and wherein the at least one mRNA is not integrated into the genome of the cell.

14. The method of claim 1, wherein the homogenous aggregates comprise at least 70% of cells expressing at least one pluripotency marker.

* * * * *